US011274333B2

(12) United States Patent
Zheng et al.

(10) Patent No.: US 11,274,333 B2
(45) Date of Patent: Mar. 15, 2022

(54) COMPOSITIONS AND METHODS FOR PREPARING SEQUENCING LIBRARIES

(71) Applicant: Molecular Cloning Laboratories (MCLAB) LLC, South San Francisco, CA (US)

(72) Inventors: Jianping Zheng, Brisbane, CA (US); Changping Shi, San Francisco, CA (US); Dan Shen, San Bruno, CA (US); Thang Nguyen, San Francisco, CA (US)

(73) Assignee: Molecular Cloning Laboratories (MCLAB) LLC, South San Francisco, CA (US)

( * ) Notice: Subject to any disclaimer, the term of this patent is extended or adjusted under 35 U.S.C. 154(b) by 1109 days.

(21) Appl. No.: 15/165,543

(22) Filed: May 26, 2016

(65) Prior Publication Data

US 2016/0348152 A1  Dec. 1, 2016

Related U.S. Application Data

(60) Provisional application No. 62/218,906, filed on Sep. 15, 2015, provisional application No. 62/167,892, filed on May 29, 2015.

(51) Int. Cl.
*C12Q 1/6869* (2018.01)
*C12Q 1/6806* (2018.01)
*C12Q 1/6874* (2018.01)

(52) U.S. Cl.
CPC ......... *C12Q 1/6806* (2013.01); *C12Q 1/6874* (2013.01)

(58) Field of Classification Search
None
See application file for complete search history.

(56) References Cited

U.S. PATENT DOCUMENTS

| | | |
|---|---|---|
| 5,766,891 A | 6/1998 | Shuman |
| 6,653,106 B1 | 11/2003 | Shuman et al. |
| 7,026,141 B2 | 4/2006 | Shuman |
| 7,078,501 B2 | 7/2006 | Heyman et al. |
| 7,803,550 B2 | 9/2010 | Makarov et al. |
| 2002/0068290 A1 | 6/2002 | Yarovinsky |
| 2006/0160072 A1 | 7/2006 | Shuman |
| 2010/0167954 A1 | 7/2010 | Earnshaw et al. |
| 2012/0316074 A1 | 12/2012 | Saxonov |

FOREIGN PATENT DOCUMENTS

| | | |
|---|---|---|
| GB | WO1998/044151 A1 | 10/1998 |
| GB | WO2000/018957 A1 | 4/2000 |
| GB | WO2008/015396 A2 | 2/2008 |
| WO | WO1996/019497 A1 | 6/1996 |
| WO | WO1998/056943 A1 | 12/1998 |
| WO | WO2001/62943 A1 | 8/2001 |
| WO | WO2013/112923 A1 | 8/2013 |

OTHER PUBLICATIONS

Heyman et al. (Genome Research 9:383-92) (Year: 1999).*
Goodchild, J., Conjugates of oligonucleotides and modified oligonucleotides: a review of their synthesis and properties. Bioconjugate Chemistry 1(3):165-87, 1990.
Berger, J., Structure of DNA topoisomerases, Biochim Biophys Acta 1400(1-3):3-18, 1998.
Cheng, C., et al., Conservation of structure and mechanism between eukaryotic topoisomerase I and site-specific recombinases, Cell 92(8):841-50, 1998.
Caron, P. and Wang, J., Appendix II: Alignment of primary sequences of DNA topoisomerases, Adv Pharmacol 29B:271-97, 1994.
Gupta, M., et al., Eukaryotic DNA topoisomerases I, Biochim Biophys Acta 1262(1):1-14, 1995.
Shuman, S., Vaccinia virus DNA topoisomerase: a model eukaryotic type IB enzyme, Biochim Biophys Acta 1400 (1-3):321-37, 1998.
Petersen, B., et al., Characterization of a DNA topoisomerase encoded by Amsacta moore entomopoxvirus, Virology 230(2):197-206, 1997.
Shuman, S. and Moss, B., Identification of a vaccinia virus gene encoding a type I Dna topoisomerase, Proc Natl Acad Sci, USA 84:7478-82, 1987.
Shuman, S., Novel approach to molecular cloning and polynucleotide synthesis using vaccinia DNA topoisomerase, J Biol Chem 269(51):32678-84, 1994.
Roca, J. and Wang, J., The capture of a DNA double helix by an ATP-dependent protein clamp: a key step in DNA transport by type II DNA topoisomerase, Cell 71(5):833-40, 1992.
Wang, J., DNA Topoisomerases: Why So Many?, J Biol Chem 266(11):6659-62, 1991.
Andersen, A., et al., Studies of the topoisomerase II—mediated cleavage and religation reactions by use of a suicidal double-stranded DNA substrate, J Biol Chem 266(14):9203-10, 1991.
Shuman, S., Site-specific interaction of vaccinia virus topoisomerase I with duplex DNA. Minimal DNA substrate for strand cleavage in vitro, J Biol Chem 266(17): 1372-79.
Margulies, M., et al., Genome sequencing in microfabricated high-density picolitre reactiors, Nature 437 (7057):376-80, 2005.
Shendure, J., et al., Accurate multiplex polonyt sequencing of an evolved bacterial genome, Science 309 (5741):1728-32, 2005.
Metzker, M., Sequencing technologies—the next generation, Nat Rev Genet 11(1):31-46, 2010.
Alnemri, E. and Litwack, G., Activation of internucleosomal DNA cleavage in human CEM lymphocytes by glucocorticoid and novobiocin Evidence for non-Ca2(+)-requiring mechanisms, J Biol Chem 265(28):17323-33, 1990.

(Continued)

*Primary Examiner* — Christopher M Gross
(74) *Attorney, Agent, or Firm* — FisherBroyles, LLP; Jill A. Jacobson

(57) ABSTRACT

Compositions comprising activated topoisomerase adaptors (TOPO-adaptors) and methods of using the activated TOPO-adaptors are provided for preparing a library of target DNA duplexes derived from sample polynucleotides (e.g., DNA, RNA) for the streamlined preparation of a large number of samples. Such libraries may be used for Next Generation Sequencing (NGS).

7 Claims, 9 Drawing Sheets

Specification includes a Sequence Listing.

(56) References Cited

OTHER PUBLICATIONS

Richards, O. and Boyer, P., Chemical Mechanism of Sonic, Acid, Alkaline and Enzymatic Degradation of DNA,, J Mol Biol 11:327-340, 1965.

Voelkerding, K., et al., Next-generation sequencing: from basic research to diagnostics, Clin Chem 55:641-58, 2009.

Pareek, C., et al., Sequencing technologies and genome sequencing, J Appl Genetics 52(4):413-435, 2011.

Mardis, E.., Next-generation DNA sequencing methods, Annu Rev Genomics Hum Genet 9:387-402, 2008.

Soni, G. and Meller, A., Progress toward ultrafast DNA sequencing using solid-state nanopores, Clin Chem 53(11):1996-2001, 2007.

Shuman, S. and Prescott, J., Specific DNA cleavage and binding by vaccinia virus DNA topoisomerase I, J Biol Chem 265(29):17826-36, 1990.

Bermans, H., et al., Next generation sequencing technology: Advances and applications, Biochemica et Biophysica Acta, 2004, 1842(10):1932-1941.

Rohland, N., et al., Cost-effective, high-throughput DNA sequencing libraries for multiplexed target capture, Genome Research, 2012, 22(5):939-946.

Van Dijk, E., et al., Library preparation methods for next-generation sequencing: Tone down the bias, Experimental Cell Research, 2014, 322(1):12-20.

* cited by examiner

100ng 350 BP LAMBDA LIBRARY PREPARED WITH ILLUMINIA TRUSEQ NANO KIT

100ng 350 BP LAMBDA LIBRARY PREPARED WITH MCLAB TOPO LIGATION LIB PREP KIT

COMPOSITIONS AND METHODS FOR PREPARING SEQUENCING LIBRARIES

CROSS-REFERENCE TO RELATED APPLICATIONS

This application claims the benefit of U.S. Provisional Application No. 62/167,892, filed on May 29, 2015, and 62/218,906, filed on Sep. 15, 2015, both of which are incorporated by reference herein in their entireties.

SEQUENCE LISTING

The instant application contains a Sequence Listing which has been submitted electronically in ASCII format and is hereby incorporated by reference in its entirety. Said ASCII copy, created on May 16, 2016, is named 05185.001 US1_SL.txt and is 9,159 bytes in size.

TECHNICAL FIELD

Compositions and methods are provided for preparing DNA libraries for sequencing by Next Generation Sequencing methods. Sequencing adaptors are provided to improve the yield of library DNA and to expedite the process of library preparation.

BACKGROUND

The advent of Next Generation Sequencing (NGS) methods generates massive amounts of nucleotide sequence information that can be used to provide sequence analysis relating to genetic information. Fundamental to NGS sequencing is library construction, which is the preparation of target polynucleotides, RNA and/or DNA, which are to be analyzed, into a form that is compatible with the sequencing system to be used.

The process of preparation of sequencing libraries can impact significantly the quality and the output of sequencing data. Current methods for preparing DNA libraries for NGS are time consuming, prone to significant sample loss, and result in low coverage of the genetic material that is being sequenced.

There exists a need for improved methods for preparing polynucleotide DNA libraries. Methods that can be utilized for desired applications, e.g., genome sequencing, targeted sequencing, RNA sequencing, etc., and that are applicable to analysis of target polynucleotides using different NGS platforms, would provide additional advantages.

BRIEF SUMMARY OF THE INVENTION

Compositions comprising activated topoisomerase adaptors (TOPO-adaptors) and methods of using the activated TOPO-adaptors are provided for preparing a library of target DNA duplexes derived from sample polynucleotides (e.g., DNA, RNA) for the streamlined preparation of a large number of samples for Next Generation Sequencing (NGS). In addition, this high-throughput method can be automated to further reduce the time and cost for providing genetic sequence analysis of large numbers of samples.

Use of activated TOPO-adaptors is advantageous in reducing and/or preventing the formation of adaptor dimers during preparation of the library. Additionally, use of activated TOPO-adaptors expedites the process of sample analysis, and greatly improves the yield of library DNA product when compared to the time taken and the yield of library product obtained using ligase-only dependent linkage of standard oligonucleotide adaptors, e.g., Illumina's TruSeq Nano DNA Library Prep.

The compositions and methods provided are applicable to analyses of samples in the fields of medicine, noninvasive diagnostics, e.g., prenatal diagnostics, agricultural and environmental monitoring, and other biological sample testing applications, that require sequencing of genetic material.

In one aspect, provided is a method for preparing a sequencing library of target DNA duplexes. In one embodiment, the method comprises (a) providing a plurality of target DNA duplexes having a first end and a second end; (b) optionally, blunt-ending and dephosphorylating the target DNA duplexes; (c) providing a plurality of first and second linear topoisomerase (TOPO)-activated sequencing adaptors, wherein the first activated TOPO-adaptors comprise a first primer binding sequence and the second adaptors comprise a second primer binding sequence, wherein the first primer binding sequence differs from the second primer binding sequence, and the first primer binding sequence hybridizes to a first oligonucleotide primer, and the second primer binding sequence hybridizes to a second oligonucleotide primer; and (d) covalently linking the first and second activated TOPO adaptors to the first and second ends of the plurality of DNA duplexes to provide a plurality of TOPO-adaptor-DNA duplex complexes, thereby preparing the sequencing library. In some embodiments, the first linear TOPO-activated sequencing adaptors each comprises complementary sequences SEQ ID NOs:2 and 3; and the second linear TOPO-activated sequencing adaptors each comprises complementary sequences SEQ ID NOs:4 and 6. In some embodiments, the first linear activated TOPO adaptors are covalently linked to the first ends of the DNA duplexes and then the second linear activated TOPO adaptors are covalently linked to the second ends of the DNA duplexes in a two step process.

In another embodiment, the method for preparing a sequencing library of target DNA duplexes comprises: (a) providing a plurality of the target DNA duplexes having a first end and a second end; (b) optionally blunt-ending and dephosphorylating the target DNA duplexes; (c) providing a plurality of partially complementary TOPO-activated sequencing adaptors, wherein the adaptors comprise a duplex region comprising a bound TOPO and at least one single stranded region, and wherein the adaptors comprise a first oligonucleotide primer binding sequence that hybridizes a first oligonucleotide primer; (d) covalently linking the TOPO-activated sequencing adaptors to the first and second ends of the plurality of DNA duplexes to provide a plurality of TOPO-adaptor-DNA duplex complexes; (e) extending the first oligonucleotide primer to generate a complementary strand that comprises a second primer binding site that hybridizes a second oligonucleotide primer; and (f) hybridizing the second oligonucleotide primer to the second primer binding site to extend a second strand of the adaptor-DNA duplex, thereby preparing the sequencing library. Target DNA duplexes may be optionally blunt-ended, for example, with a T4 polymerase and/or Klenow DNA polymerase. Target DNA duplexes may optionally be dephosphorylated, for example, with an alkaline phosphatase, e.g., calf intestinal phosphatase, shrimp alkaline phosphatase, Antarctic phosphatase.

In some embodiments, the partially complementary adaptor comprises a single-stranded hairpin region, wherein the hairpin region comprises the first oligonucleotide primer binding sequence and the reverse complement of the second primer binding site. In one embodiment, the hairpin topoisomerase (TOPO)-activated sequencing adaptors each comprises an oligonucleotide sequence of SEQ ID NO:20.

In some embodiments, the partially complementary adaptor comprises a first oligonucleotide and a second oligonucleotide, wherein portions of each of the first and second oligonucleotides are complementary to one another and form the duplex region that comprises a bound TOPO, wherein portions of each of the first and second oligonucleotides are single stranded and not complementary to one another, wherein the second oligonucleotide comprises a first primer binding sequence, and wherein the first oligonucleotide comprises the reverse complement of the second primer binding site. In one embodiment, the adaptor comprises first and second oligonucleotides of SEQ ID NOs:30 and 31, respectively. In another embodiment, the adaptor comprises first and second oligonucleotides of SEQ ID NOs:32 and 31, respectively.

In some embodiments, step (d) of the methods for preparing a sequencing library of target DNA duplexes disclosed herein comprises: (i) reacting a TOPO-bearing first strand of the activated TOPO-adaptor complex with the 5'-end of the first strand of the target DNA duplex to covalently link the first strand of the activated TOPO-adaptor to the first strand of the TOPO-adaptor-target DNA duplex complex; and (ii) ligating a second strand of the activated TOPO-adaptor complex to the 3'-end of a second strand of the target DNA duplex.

In other embodiments, the methods for preparing a sequencing library of target DNA duplexes disclosed herein further comprise: hybridizing the first and second oligonucleotide primers to the first and second oligonucleotide primer binding sequences and amplifying the TOPO-adaptor-polynucleotide complex.

In other embodiments, the step of covalently linking ends of the target DNA duplexes, e.g., end-repaired and dephosphorylated fragments of DNA, to the topoisomerase-activated sequencing adaptors in the methods disclosed herein is performed in less than 10 minutes.

In other embodiments, the methods for preparing a sequencing library of target DNA duplexes disclosed herein further comprise preparing the activated TOPO adaptors.

In other embodiments, the methods for preparing a sequencing library of target DNA duplexes disclosed herein further comprise obtaining DNA or RNA from a biological sample. In some embodiments, the biological sample is a biological fluid sample or a tissue sample.

In other embodiments, the target DNA duplexes of the methods for preparing a sequencing library are fragmented portions of genomic DNA. In other embodiments, the target DNA duplexes are fragments of cDNA transcribed from cellular RNA of a biological sample.

In another aspect, a method for next generation sequencing (NGS) of a polynucleotide is provided. In some embodiments, the method comprises: (a) preparing a sequencing library of target DNA duplexes as disclosed herein; and (b) next generation sequencing the library of TOPO-adaptor-target DNA duplex complexes. In some embodiments, the sequencing method is selected from: sequencing-by-synthesis, pyrosequencing, and sequencing-by-ligation. In other embodiments, the sequencing method is NGS of tags or of single molecules.

In another aspect, a kit is provided. In some embodiments, the kit comprises: (i) a plurality of TOPO-activated sequencing adaptors; (ii) one or more amplification primers; (iii) one or more sequencing primers; (iv) one or more reaction buffers; and (v) instructions for preparing a DNA sequencing library. In some embodiments, the TOPO-activated adaptors of the kit are complementary linear TOPO-adaptors. In some other embodiments, the TOPO-activated adaptors of the kit are partially complementary, e.g., hairpin or Y-shaped, adaptors. In yet other embodiments, the kit further comprises Uracil DNA Glycosylase (UDG). In yet other embodiments, the kit further comprises a ligase enzyme.

INCORPORATION BY REFERENCE

Figure 1:
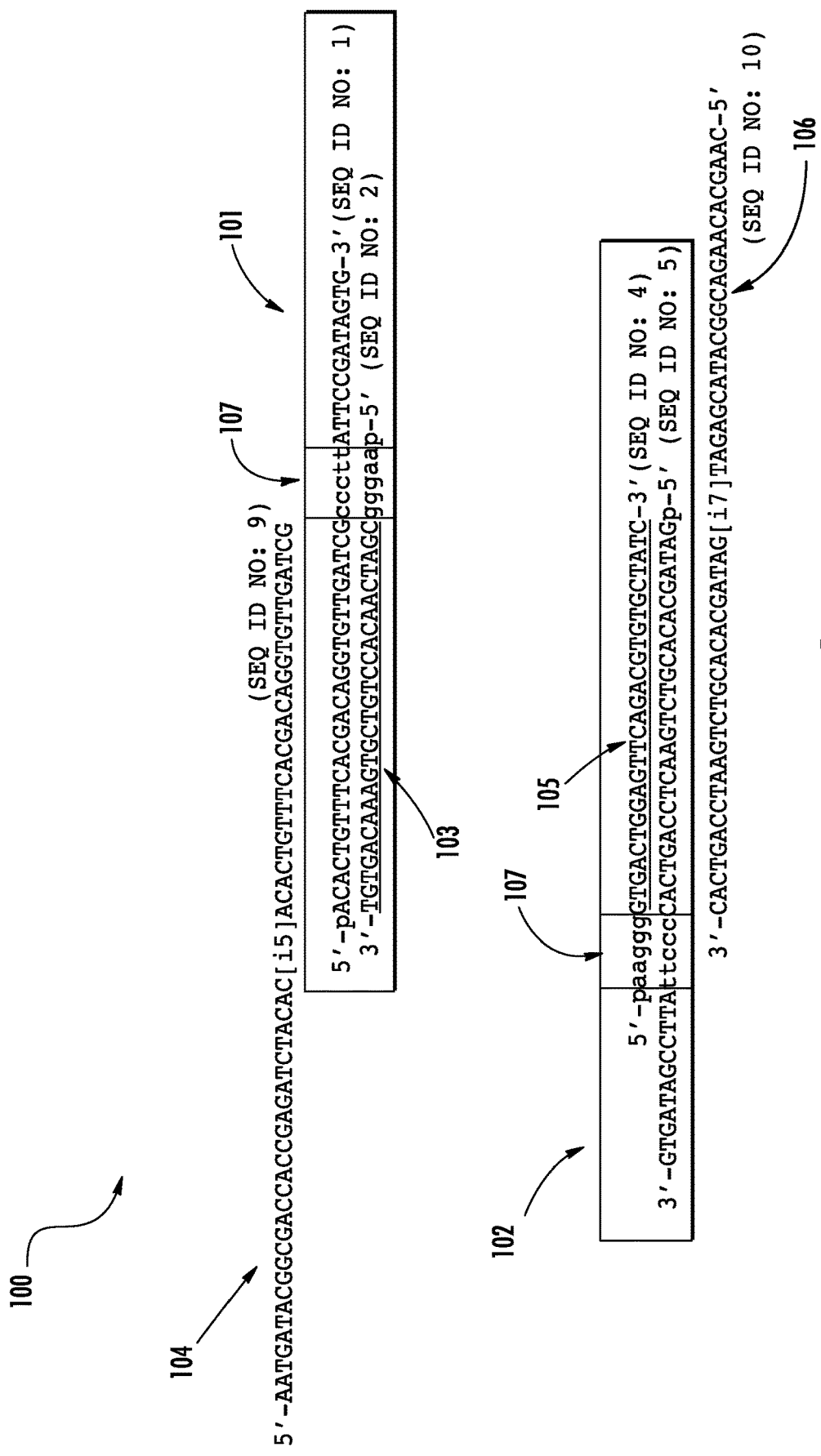
FIG. 1 illustrates an exemplary set (100) of two complementary linear pro-adaptors (101) and (102), and universal oligonucleotide primers (104) and (106). Reference is made to Example 2.

All patents, patent applications, and other publications, including all sequences disclosed within these references, referred to herein are expressly incorporated by reference, to the same extent as if each individual publication, patent or patent application was specifically and individually indicated to be incorporated by reference. However, the citation of any document is not to be construed as an admission that it is prior art with respect to the present invention.

DETAILED DESCRIPTION

Compositions comprising activated topoisomerase (TOPO) adaptors and methods of using the activated TOPO adaptors are provided for preparing a library of target DNA duplexes derived from sample polynucleotides (e.g., DNA, RNA). Such libraries may be used for the streamlined preparation of a large number of samples for applications such as, but not limited to, polynucleotide sequencing, e.g., Next Generation Sequencing (NGS). Use of TOPO adaptors for preparing libraries improves the yield of library DNA, expedites the process of library preparation, and consequently of sample analysis, and minimizes or prevents formation of adaptor dimers.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The term "duplex" herein refers to a region of complementarity that exists between two polynucleotide sequences. The term "duplex region" when used in reference to a TOPO adaptor, herein refers to the region of sequence complementarity that exists between two oligonucleotides or two portions of a single oligonucleotide that encompasses the recognition sequence for topoisomerase.

The term "target DNA duplex" herein refers to a double stranded DNA molecule that is derived from a sample polynucleotide that is DNA, e.g., genomic or cell-free DNA, and/or RNA.

The term "pro-adaptor" herein refers to a duplex oligonucleotide (e.g., DNA) substrate that a compatible site-specific topoisomerase, e.g., Topoisomerase I, can cleave and to which the topoisomerase will covalently attach at the point of cleavage to yield an activated TOPO adaptor.

The term "activated TOPO adaptor" herein refers to a polynucleotide structure comprising a duplex oligonucleotide region having a single topoisomerase covalently bound at or near the 3' terminus of a first end.

The term "a first end" and "a second end" when used in reference to a nucleic acid molecule, herein refers to ends of a linear nucleic acid molecule.

The term "single stranded overhang" or "overhang" is used herein to refer to a strand of a double stranded (ds) nucleic acid molecule that extends beyond the terminus of the complementary strand of the ds nucleic acid molecule. The term "5' overhang" or "5' overhanging sequence" is used herein to refer to a strand of a ds nucleic acid molecule that extends in a 5' direction beyond the 3' terminus of the complementary strand of the ds nucleic acid molecule. The term "3' overhang" or "3' overhanging sequence" is used herein to refer to a strand of a ds nucleic acid molecule that extends in a 3' direction beyond the 5' terminus of the complementary strand of the ds nucleic acid molecule.

The term "scissile strand" herein refers to a strand of a duplex oligonucleotide adaptor that comprises a site-specific recognition sequence for a topoisomerase ("TOPO"), e.g., topoisomerase I, e.g., a Vaccinia virus topoisomerase I, and recombinant forms thereof.

The term "library" herein refers to a collection or plurality of template molecules, i.e., target DNA duplexes, which share common sequences at their 5' ends and common sequences at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates must be related in terms of sequence and/or source.

The term "Next Generation Sequencing (NGS)" herein refers to sequencing methods that allow for massively parallel sequencing of clonally amplified and of single nucleic acid molecules during which a plurality, e.g., millions, of nucleic acid fragments from a single sample or from multiple different samples are sequenced in unison. Non-limiting examples of NGS include sequencing-by-synthesis, sequencing-by-ligation, real-time sequencing, and nanopore sequencing.

The term "bioassay" herein refers to a multistep assay that includes NGS sequencing of the sample nucleic acids, e.g., DNA. Multistep bioassays can comprise one or more of the steps of sample collection, sample fractionation, nucleic acid purification, and the requisite nucleic acid modification steps for the preparation of sequencing libraries.

The term "end-repaired DNA" herein refers to DNA that has been subjected to enzymatic reactions in vitro to blunt-end 5'- and/or 3'-overhangs. Blunt ends can be obtained by filling in missing bases for a strand in the 5' to 3' direction using a polymerase, and by removing 3'-overhangs using an exonuclease. For example, T4 polymerase and/or Klenow DNA polymerase may be used for DNA end repair.

The term "sequencing library" herein refers to DNA that is processed for sequencing, e.g., using massively parallel methods, e.g., NGS. The DNA may optionally be amplified to obtain a population of multiple copies of processed DNA, which can be sequenced by NGS.

The term "adaptor" herein refers to a nucleic acid that is attached to both strands of a double-stranded DNA molecule. The adaptor can be composed of two distinct oligonucleotide molecules that are base-paired with one another, i.e., complementary. Alternatively, the adaptor can be composed of a single oligonucleotide that comprises one or more regions of complementarity, and one or more non-complementary regions.

The term "base pair" or "bp" as used herein refers to a partnership (i.e., hydrogen bonded pairing) of adenine (A) with thymine (T), or of cytosine (C) with guanine (G) in a double stranded DNA molecule. In some embodiments, a base pair may comprise A paired with Uracil (U), for example, in a DNA/RNA duplex.

The term "complementary" herein refers to the broad concept of sequence complementarity in duplex regions of a single polynucleotide strand or between two polynucleotide strands between pairs of nucleotides through base-pairing. It is known that an adenine nucleotide is capable of forming specific hydrogen bonds ("base pairing") with a nucleotide, which is thymine or uracil. Similarly, it is known that a cytosine nucleotide is capable of base pairing with a guanine nucleotide.

The term "essentially complementary" herein refers to sequence complementarity in duplex regions of a single polynucleotide strand or between two polynucleotide strands of an adaptor wherein the complementarity is less than 100% but is greater than 90%, and retains the stability of the duplex region under conditions for covalent linking of the adaptor to a target DNA duplex.

The term "purified" herein refers to a molecule is present in a sample at a concentration of at least 90% by weight, or at least 95% by weight, or at least 98% by weight of the sample in which it is contained.

The term "isolated" herein refers to a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, e.g., via chromosomal expression, but the nucleic acid molecule is present extrachromasomally or at a chromosomal location that is different from its natural chromosomal location.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of polymeric operatively linked nucleotides is typically referred to herein as a "base sequence," "nucleotide sequence," or nucleic acid or polynucleotide "strand," and is represented herein by a formula whose left to right orientation is in the conventional direction of 5'-terminus to 3'-terminus, referring to the terminal 5' phosphate group and the terminal 3' hydroxyl group at the "5'" and "3'" ends of the polymeric sequence, respectively.

The terms "oligonucleotide", "polynucleotide" and "nucleic acid" herein refer to a molecule including two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning or from a natural (e.g., genomic) source. As used herein, the term "polynucleotide" refers to a polymer molecule composed of nucleotide monomers covalently bonded in a chain. DNA (deoxyribonucleic acid) and RNA (ribonucleic acid) are examples of polynucleotides.

The term "primer" herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and a polymerase enzyme, e.g., a thermostable enzyme, in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the polymerase, e.g., thermostable polymerase enzyme. The exact lengths of a primer will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

As used herein, the term "index" when used in reference to a nucleotide sequence is intended to mean a unique nucleotide sequence that is distinguishable from other indices as well as from other nucleotide sequences within polynucleotides contained within a sample. A nucleotide index can be a random or a specifically designed nucleotide sequence. An index can be of any desired sequence length so long as it is of sufficient length to be a unique nucleotide sequence within a plurality of indices in a population and/or within a plurality of polynucleotides that are being analyzed or interrogated. A nucleotide index of the disclosure is useful, for example, to be attached to a target polynucleotide to tag or mark a particular species for identifying all members of the tagged species within a population. Accordingly, an index is useful as a "barcode" where different members of the same molecular species can contain the same index and where different species within a population of different polynucleotides can have different indices. For example, index sequences can be incorporated into a polynucleotide, e.g., target DNA, during sequencing library preparation for multiplex sequencing of pooled libraries prepared from different sources.

The term "synthesis" herein refers to any in vitro method for making a new strand of polynucleotide or elongating an existing polynucleotide (i.e., DNA or RNA) in a template dependent manner. Synthesis, according to the invention, can include amplification, which increases the number of copies of a polynucleotide template sequence with the use of a polymerase. Polynucleotide synthesis (e.g., amplification) results in the incorporation of nucleotides into a polynucleotide (e.g., extension from a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, polymerase chain reaction (PCR), and may include the use of labeled nucleotides, e.g., for probes and oligonucleotide primers, or for polynucleotide sequencing.

The term "template DNA molecule" herein refers to a strand of a nucleic acid from which a complementary nucleic acid strand is synthesized by a DNA polymerase, for example, in a primer extension reaction.

The term "template-dependent manner" herein refers to a process that involves the template-dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is complementary to the template, i.e., dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

The term "at or near" when used with respect to a topoisomerase, means that the topoisomerase is covalently bound to one strand of a duplex nucleic acid molecule, e.g., TOPO adaptor, such that it can ligate the terminus of the strand to which it is bound, to a second nucleic acid molecule containing a free 5' terminal hydroxyl group. Generally, the topoisomerase is "at or near" an end by virtue of being covalently bound to one terminus of the end. For example, where the topoisomerase is a type IB topoisomerase such as a Vaccinia topoisomerase, the topoisomerase is bound at the 3' terminus of an end of a duplex nucleic acid molecule. However, an end having a topoisomerase covalently bound to a terminus of the end also can contain a single stranded overhang sequence in the complementary strand, thus extending beyond the terminus to which the topoisomerase is bound. Such a configuration is an example of a topoisomerase near an end of the ds nucleic acid molecule.

The headings provided herein are not limitations of the various aspects or embodiments of the invention, which can be had by reference to the specification as a whole. Accordingly, the terms defined immediately below are more fully defined by reference to the specification as a whole.

Fundamental to NGS library construction is the preparation of the nucleic acid from a biological sample, i.e. sample RNA or DNA, into a form that is compatible with the sequencing system to be used. The TOPO-adaptors provided herein can be utilized for the preparation of sequencing libraries according to the requirements of NGS platforms, for example, platforms developed by Illumina, Life Technologies, Roche, and Pacific Biosciences.

In general, the core steps in preparing RNA or DNA for NGS analysis are: (i) fragmenting and/or sizing the sample polynucleotides to a desired length, (ii) if the sample is single-stranded, converting fragmented sample polynucleotides to double-stranded DNA, (iii) attaching oligonucleotide adaptors to the ends of target fragments, (iv) amplifying the adaptor-fragment complexes, and (iv) quantifying the final library product for sequencing.

In current methods for preparing sequencing libraries for NGS, the step (iii) of attaching oligonucleotide adaptors to the ends of target fragments typically requires that the sample polynucleotide that has been converted to double-stranded DNA undergo (a) end-repair of the duplex strands, (b) phosphorylation of the 5'-ends, (c) A-tailing of the 3'-ends to facilitate ligation to sequencing adaptors, (f) ligase-only-dependent ligation of adaptors to the fragmented DNA duplexes, and optionally (g) limited amplification to enrich for product that has adaptors ligated to both ends, i.e., the adaptor-target DNA duplex-adaptor product. Current methods are time consuming and inefficient in providing acceptable yields of DNA library product. Additionally, another major drawback in preparing nucleic acid fragment libraries by ligating adaptors to the ends of template nucleic acid fragments is the formation of adaptor-dimers. Adaptor-dimers are formed by the ligation of two adaptors directly to each other such that they do not contain a template nucleic acid fragment as an insert. Such molecules are undesirable, in that during any amplification steps, for example during a universal amplification reaction, adaptor-dimers are amplified alongside the nucleic acid fragment library. Since adaptor-dimers are generally smaller than the fragments contained in the libraries they amplify and accumulate at a faster rate. This reduces the efficiency of the amplification reaction by limiting amplification of the library fragments due to depletion of components, such as for example dNTP's and primers, in the amplification reaction. Another more serious concern that when such amplified fragments are sequenced they do not give useful sequence information since they contain no insert. In the case of clustered arrays, a significant population of clusters that have no target DNA sequence is undesirable due to the lower density of real sequence data obtained from a chip of finite size. Hence the efficiency of sequencing can be significantly reduced. Thus, the preparation of libraries with a low level of adaptor-dimers is highly advantageous in the sequencing of polynucleotides, particularly when such processes are high-throughput.

The TOPO-adaptor compositions and methods of using the TOPO-adaptors for preparing a sequencing library as provided herein require dephopshorylation of the 5'-ends, exclude A-tailing of the 3'-ends, and utilize topoisomerase catalyzed linking of adaptors. Alternatively, the methods utilize a combination of ligase and topoisomerase for catalyzing the linking of the adaptors to target DNA. This methodology significantly reduces the time typically taken for the step of adaptor attachment from a range of about 4 to 0.5 hours to about 10 minutes, or less. The yield of library product is also greater than that of a widely used method, e.g., Illumina's TruSeq library preparation. Additionally, activated TOPO-adaptors that are used in preparing DNA libraries according to the methods provided minimize or prevent the formation of adaptor dimers as the linking of an activated TOPO-adaptor requires the presence of a dephosphorylated acceptor DNA, which cannot be provided by a second activated TOPO-adaptor as it has a phosphorylated 5' end.

The library is formed by covalently linking activated TOPO-adaptors to each end, i.e., the 5'- and 3'-ends of a plurality of target DNA duplexes to form TOPO-adaptor-target DNA duplex-TOPO-adaptor complexes. Each TOPO-adaptor comprises at least one oligonucleotide primer binding sequence, which serves to hybridize an oligonucleotide primer to initiate a primer extension reaction that is performed to produce extension products complementary to at least one strand of each topoisomerase adaptor-sample DNA complex. The resulting primer extension products, which can optionally be subjected to limited cycle amplification, collectively provide a library of sample/target nucleic acids.

Pro-TOPO Adaptors

In some embodiments, the activated TOPO adaptors are derived from pro-adaptors that comprise a duplex oligonucleotide (e.g., DNA) region that comprises a sequence that a compatible site-specific topoisomerase can cleave e.g., C/TCCTTN (SEQ ID NOs: 12 and 13), and to which the topoisomerase will covalently attach at the point of cleavage to yield the activated TOPO sequencing adaptors described herein. In some embodiments, the duplex oligonucleotide region is formed by annealing two separate complementary oligonucleotides. In other embodiments, the oligonucleotide region is provided by two complementary portions of a single oligonucleotide.

A first strand, or scissile strand, of the duplex region of the pro-adaptors comprises a sequence that specifies a recognition sequence for a topoisomerase enzyme. The recognition sequence for the topoisomerase enzyme, e.g., Vaccinia topoisomerase, comprises a consensus pentapyrimidine element 5'-(C/T)CCTT↓N (SEQ ID NOs:12 and 13) (or related sequences) in a first strand. In some embodiments, the scissile bond is situated at least 2 bp from the 3' end of the first strand of the duplex region of the adaptor. For example, the recognition sequence can be situated in the range of 2-12 bp from the 3' end of the duplex adaptor DNA. In some embodiments, the cleavable complex formation by the topoisomerase I requires six duplex nucleotides upstream and two nucleotides downstream of the cleavage site. In some embodiments, the recognition sequence further comprises a sequence of at least 1 bp upstream of the pentapyrimidine element, i.e., the 5'-end of the recognition sequence. Examples of recognition sequences include, but are not limited to +6/−6 duplex GCCCTTATTCCC (SEQ ID NO:14), +8/−4 duplex TCGCCCTTATTC (SEQ ID NO:15), +10/−2 duplex TGTCGCCCTTAT (SEQ ID NO:16), +11/−2 duplex GTGTCGCCCTTA (SEQ ID NO:17) and +10/−12 GATTCCCCTTATTCCGATAGTG (top strand) (SEQ ID NO:18).

In some embodiments, the pro-adaptor comprises two separate oligonucleotides, a first and a second oligonucleotide strand, that are complementary at least over the sequence that specifies the topoisomerase recognition sequence. In some embodiments, the first strand, or scissile strand has a 3'-overhang of at least 2, at least 5, at least 10, at least 15, or at least 20 nucleotides. In some embodiments, a set of two pro-adaptors, a first and a second pro-adaptor, is required to provide a first and a second activated TOPO adaptor as described elsewhere herein. FIG. 1 illustrates a set of two complementary linear pro-adaptors (101) and (102), that respectively comprise a first universal primer binding sequence (103) for oligonucleotide primer (104), and a second universal primer binding sequence (105) for oligonucleotide primer (106), and a duplex region that comprises a topoisomerase recognition sequence (107). The exemplary pro-adaptors shown in FIG. 1 comprise a scissile strand that has a 3'-overhang. A portion of the 3' overhang is necessary for the topoisomerase activation of the pro-adaptor as is described elsewhere herein. In some embodiments, the pro-adaptor further comprises one or more sequences for binding sequencing primers. In some embodiments, the first oligonucleotide strand comprises the 3' overhang sequence (and ultimately the bound TOPO in the activated TOPO adaptor) and the second oligonucleotide strand comprises the primer (first primer or second primer) binding sequence.

In other embodiments, the pro-adaptor is a single oligonucleotide that comprises at least one complementary duplex region that specifies the topoisomerase recognition sequence, and at least one non-complementary region. In some embodiments, a first strand, the scissile strand of the duplex region of the oligonucleotide pro-adaptor comprises a 3'-overhang. The 3'-overhang is at least 2, at least 5, at least 10, at least 15, or at least 20 nucleotides. In some embodiments, a set of two pro-adaptors, a first and a second pro-adaptor, is required to provide a first and a second activated TOPO adaptor as described elsewhere herein.

Figure 2:
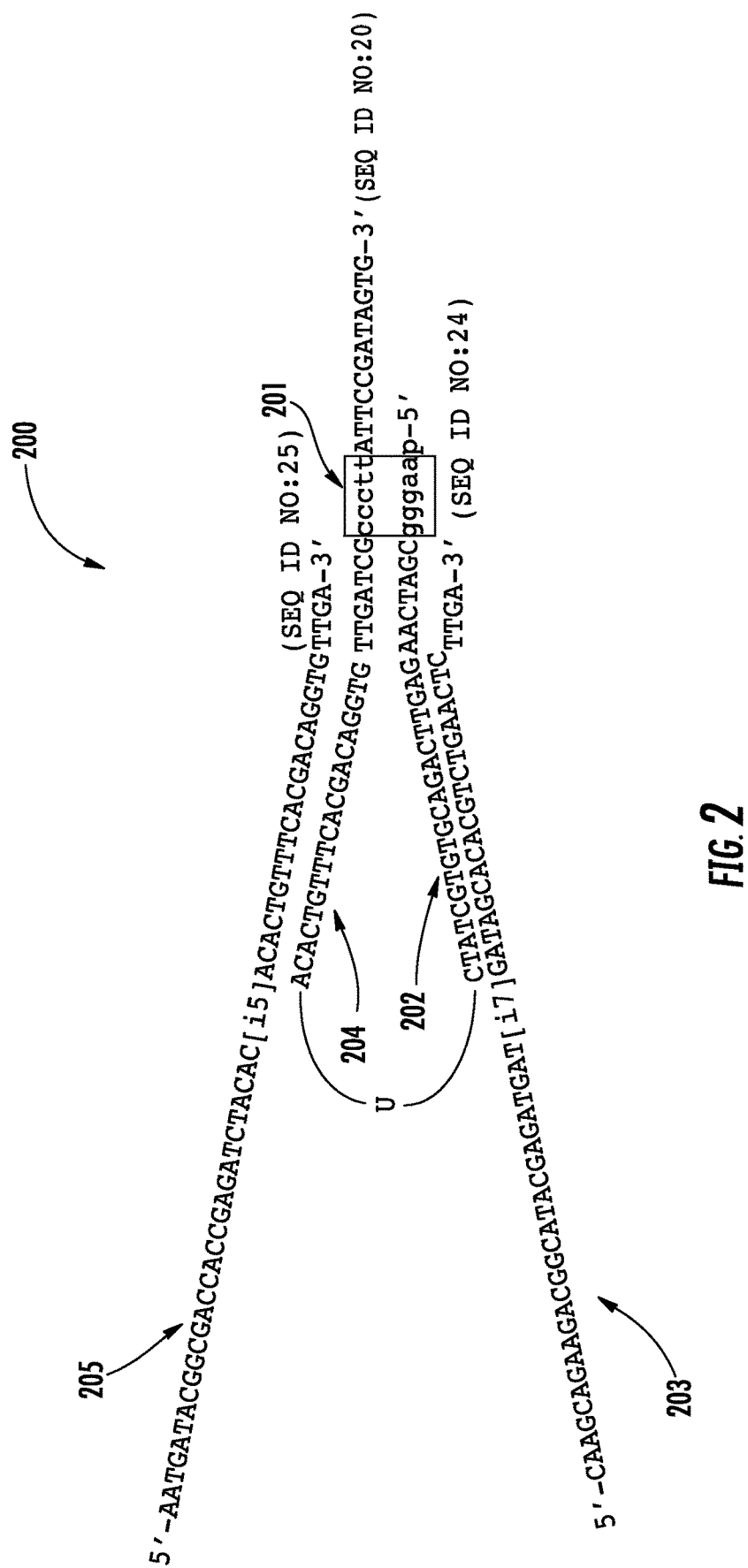
FIG. 2 illustrates an exemplary partially complementary hairpin pro-adaptor (200), and universal oligonucleotide primers (203) and (205).

FIG. 2 illustrates an exemplary partially complementary hairpin pro-adaptor (200), which is formed by a single oligonucleotide that comprises a topoisomerase recognition sequence (201) within its duplex region, a first universal primer binding sequence (202) to which a first oligonucleotide primer (203) can hybridize, and a second sequence (204) whose reverse complement generates the second oligonucleotide primer binding sequence to which a second oligonucleotide primer (205) can hybridize. In one embodiment, a partially complementary oligonucleotide pro-adaptor comprises a single oligonucleotide of SEQ ID NO:20. The single oligonucleotide pro-adaptor comprises two portions that are complementary and specify a topoisomerase-I recognition sequence CCCTTN (SEQ ID NO:12) where N is A. The single oligonucleotide pro-adaptor further comprises a first universal primer binding sequence of SEQ ID NO:21, and a second sequence (SEQ ID NO:22) whose reverse complement generates the second oligonucleotide primer binding sequence (SEQ ID NO:23). Oligonucleotide primers of SEQ ID NOs: 24 and 25, respectively bind to SEQ ID NOs:21 and 23 in initial primer extension reactions and subsequent amplification of the extended products. The first and second oligonucleotide primer binding sequences are separated by a cleavable uracil base. The [i5] and [i7] inserts within the oligonucleotide primers as shown in FIG. 2 indicate the position where an index sequence can be introduced into the oligonucleotide primers.

Figure 7:
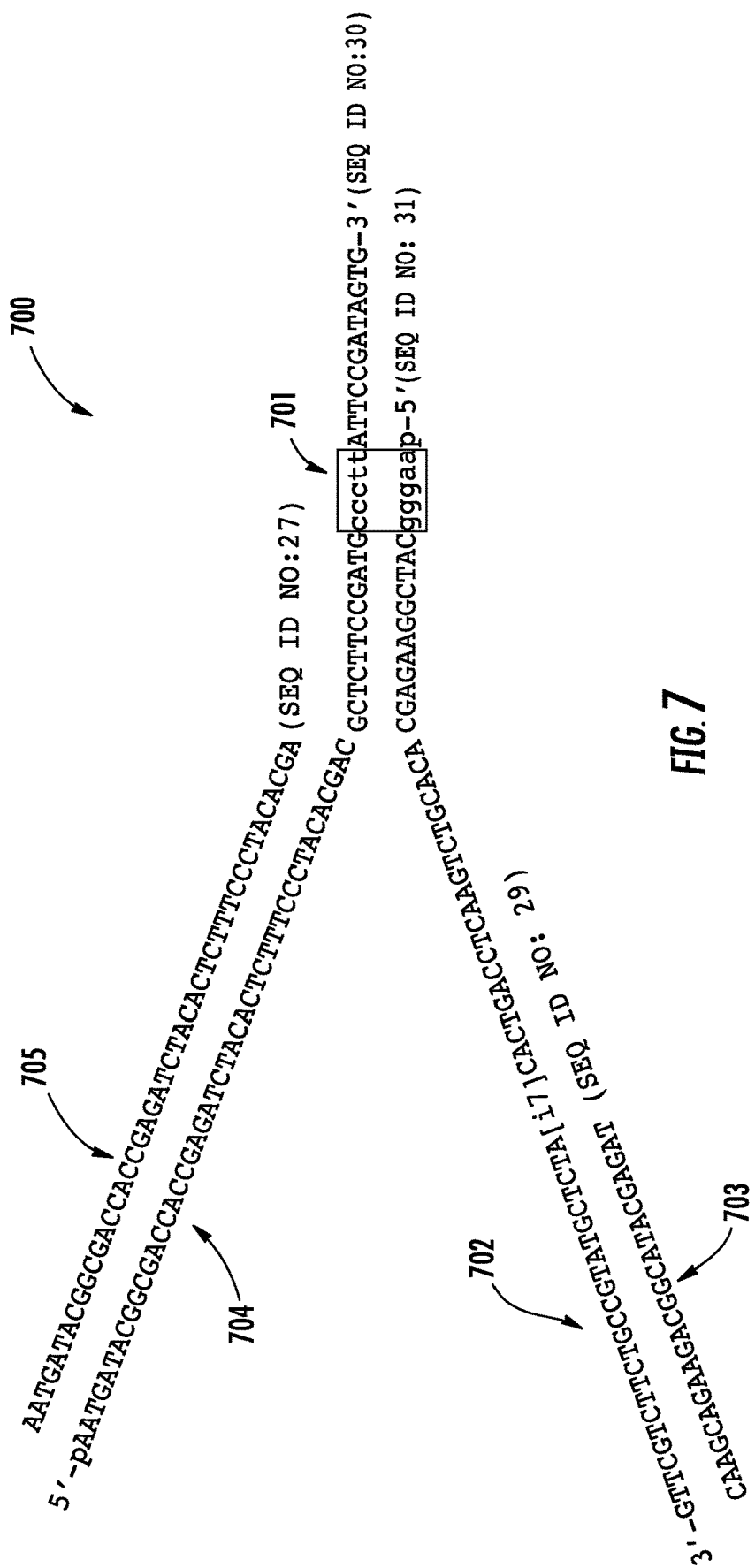
FIG. 7 illustrates an exemplary partially complementary "single index" pro-adaptor (700), and universal oligonucleotide primers (703) and (705).

FIG. 7 illustrates an exemplary partially complementary "Y-shaped" pro-adaptor (700), which is formed by first and second oligonucleotides that comprises a topoisomerase recognition sequence (701) within a duplex region, a first primer binding sequence (702) in the non-complementary (non-duplex) region of the second oligonucleotide to which a first oligonucleotide primer (703) can hybridize, and a second sequence in the non-complementary region of the first oligonucleotide (704) whose reverse complement generates a second oligonucleotide primer binding sequence to which a second oligonucleotide primer (705) can hybridize. In one embodiment, depicted in FIG. 7, a partially complementary oligonucleotide pro-adaptor comprises first and second oligonucleotides having the sequences depicted in SEQ ID NOs:30 and 31, respectively. The two oligonucleotides of the pro-adaptor comprise portions that are complementary and that specify a topoisomerase-I recognition sequence CCCTTN (SEQ ID NO:12) where N is A. The pro-adaptor further comprises a first primer binding sequence depicted in SEQ ID NO:33, and a second sequence (SEQ ID NO:27) whose reverse complement generates the second oligonucleotide primer binding sequence (SEQ ID NO:34). A first primer depicted in SEQ ID NO: 29 binds to SEQ ID NO:32 in an initial primer extension reaction, and first and second primers with sequences depicted in SEQ ID NOs: 29 and 27, respectively, are used for subsequent amplification of the extended products. The [i7] insert within the second oligonucleotide as shown in FIG. 7 indicates the position where an index sequence can be introduced into the amplification products.

Figure 8:
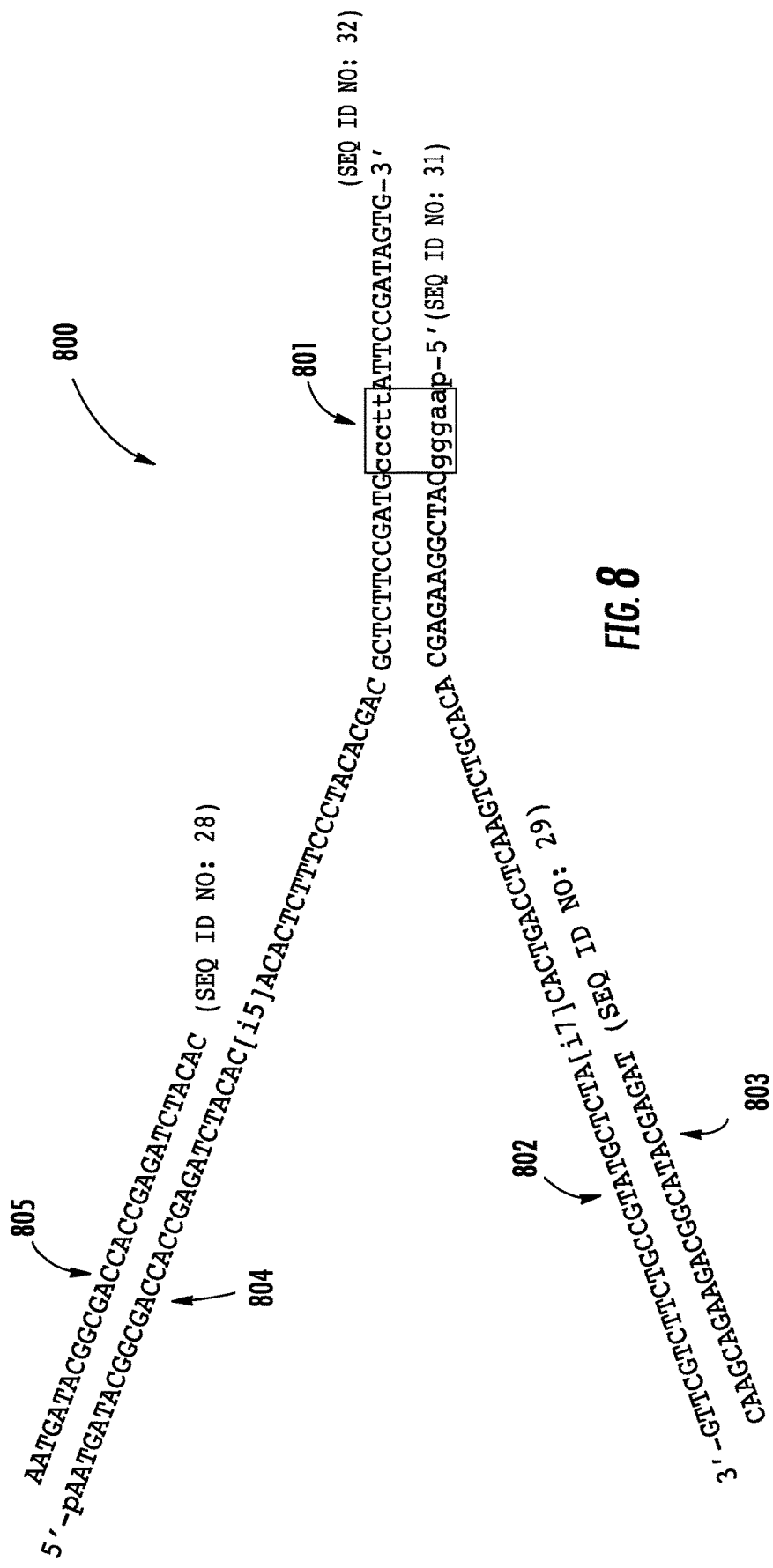
FIG. 8 illustrates an exemplary partially complementary "dual index" pro-adaptor (800), and universal oligonucleotide primers (803) and (805).

FIG. 8 illustrates an exemplary partially complementary "Y-shaped" pro-adaptor (800), which is formed by first and second oligonucleotides that comprises a topoisomerase recognition sequence (801) within a duplex region, a first primer binding sequence (802) in the non-complementary (non-duplex) region of the second oligonucleotide to which a first oligonucleotide primer (803) can hybridize, and a second sequence in the non-complementary region of the first oligonucleotide (804) whose reverse complement generates a second oligonucleotide primer binding sequence to which a second oligonucleotide primer (805) can hybridize. In one embodiment, depicted in FIG. 8, a partially complementary oligonucleotide pro-adaptor comprises first and second oligonucleotides having the sequences depicted in SEQ ID NOs:32 and 31, respectively. The two oligonucleotides of the pro-adaptor comprise portions that are complementary and that specify a topoisomerase-I recognition sequence CCCTTN (SEQ ID NO:12) where N is A. The pro-adaptor further comprises a first primer binding sequence depicted in SEQ ID NO:33, and a second sequence (SEQ ID NO:27) whose reverse complement generates the second oligonucleotide primer binding sequence (SEQ ID NO:35). A first primer depicted in SEQ ID NO: 29 binds to SEQ ID NO:32 in an initial primer extension reaction, and first and second primers with sequences depicted in SEQ ID NOs: 29 and 28, respectively, are used for subsequent amplification of the extended products. The [i5] and [i7] inserts within the first and second oligonucleotide, respectively as shown in FIG. 8 indicate the positions where index sequences can be introduced into the amplification products.

In some embodiments, the pro-adaptors further comprise one or more sequences for binding sequencing primers.

In some embodiments, a portion of first and/or second oligonucleotide primer(s) is necessary for annealing to the primer binding sequences specified by the adaptor. In some embodiments, the length of the portion of the oligonucleotide primer that binds to the adaptor sequence is between 5 and 50, between 10 and 40, or between 20 and 30 nucleotides. In other embodiments, the length of the portion of the oligonucleotide primer that binds to the adaptor sequence is any of about 10, 20, 25, 30, 35, 40, 45, or 50 nucleotides, or any of at least about 10, 20, 30, 35, 40, 45, or 50 nucleotides.

Generally, it is advantageous for the duplex oligonucleotide region of the adaptor to be as short as possible without loss of function. By 'function' in this context is meant that the double-stranded region form a stable duplex under standard reaction conditions for a topoisomerase and ligase-catalyzed nucleic acid ligation reaction, which will be well known to the skilled reader (e.g., incubation at a temperature in the range of from 16° C. to 25° C. in a buffer appropriate for the enzymes), such that the two strands forming the adaptor remain partially annealed during ligation of the adaptor to a target DNA duplex. It is not absolutely necessary for the duplex region of the adaptor to be stable under the conditions typically used in the annealing steps of primer extension or PCR reactions. Generally, it is preferred for the duplex region to be 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs. It is preferred, but not absolutely essential, for the two strands of the adaptor to be 100% complementary in the duplex region. It will be appreciated that one or more nucleotide mismatches may be tolerated within the double-stranded region, provided that the two strands are capable of forming a stable duplex under standard ligation conditions. Adaptors for use in the invention will generally include a duplex region forming the 'ligatable' end of the adaptor, i.e., the end that is joined to a target DNA duplex in the ligation reaction. In some embodiments, the ligatable end of the adaptor may be blunt. In other embodiments, the ligatable end of the adaptor may comprise short 5' or 3' overhangs of one or more nucleotides, which may be present to facilitate/promote ligation. In yet other embodiments, the adaptor comprises a single nucleotide overhang. For example, the single nucleotide overhang can be a thymidine. The 5' terminal nucleotide at the ligatable end of the adaptor should be phosphorylated to enable phosphodiester linkage to a 3' hydroxyl group on the target polynucleotide.

The oligonucleotide adaptors may be composed of conventional deoxyribonucleotide or ribonucleotide units or modified synthetic oligonucleotide structures. It is further understood that the invention is not limited to oligonucleotide adaptor compositions comprised of conventional deoxyribonucleotide or ribonucleotide units. Modifications to the oligonucleotide may be made at the bases, the sugars, the ends of the chain, or at the phosphate groups of the backbone. Alterations of the bases or sugars must be designed so as to avoid disrupting hydrogen bonding critical to essential oligonucleotide base pairing interactions. Modification to the ends and backbone of the molecule are generally easier to effect and these sites provide a convenient point for attachment of the functional groups discussed above. Chemically modified phosphate backbones for use in the oligonucleotides of the invention include methylphosphonates, phosphotriesters, phosphorothioates and phosphoramidates (see Goodchild (1990) *Bioconjugate Chemistry* 1: 165-187 for review). The selection of appropriate phosphate backbone modifications for use in the invention will be directed by the intended use of the adaptor or adaptor-target nucleic acid topoisomerase ligation product. Considerations include required chemical and biological stability and lipophilic properties. Advantages of particular modified phosphate groups are well known in the art and have been reviewed in detail (see Goodchild (1990), supra.

Activation of Pro-TOPO-Adaptors

Activation of pro-adaptors generally occurs by incubating the pro-adaptor with a site-specific topoisomerase under suitable conditions, that will cause the enzyme to cleave the duplex DNA of the pro-adaptor at the cleavage site, and covalently attach to the 3' end of the cleavage site therein, forming an activated TOPO adaptor. Other than these requirements, there is no restriction placed on the number or composition (i.e., nucleotide sequence) of the two oligonucleotides in the duplex adaptor region, except that they must be selected so that the two oligonucleotides or oligonucleotide portions of a single oligonucleotide will anneal and remain annealed during attachment of the topoisomerase to the pro-adaptor. The length and nucleotide composition of the two oligonucleotides or oligonucleotide portions of the single oligonucleotide can be selected for convenience to avoid unwanted effects that might result from incorporating into the linker an undesirable endonuclease site. Exemplary conditions for activation are known in the art and can be found in U.S. Pat. No. 5,766,891, the contents of which are incorporated by reference herein.

Topoisomerases are a class of enzymes that modify the topological state of DNA via the breakage and rejoining of DNA strands (Shuman et al., U.S. Pat. No. 5,766,891, incorporated herein by reference). Topoisomerases are categorized as type I, including type IA and type IB topoisomerases, which cleave a single strand of a double stranded nucleic acid molecule, and type II topoisomerases (gyrases), which cleave both strands of a nucleic acid molecule. As disclosed herein, type I and type II topoisomerases, as well as catalytic domains and mutant forms thereof, are useful for generating activated-TOPO adaptors provided herein. Type II topoisomerases have not generally been used for generating recombinant nucleic acid molecules or cloning procedures, whereas type IB topoisomerases, are used in a variety of procedures.

In some embodiments, activated-TOPO adaptors are generated by reacting a Type IA topoisomerase with a pro-adaptor. In other embodiments, activated-TOPO adaptors are generated by reacting a Type IB topoisomerase with a pro-adaptor. In yet other embodiments, activated-TOPO adaptors are generated by reacting a Type II topoisomerase with a pro-adaptor.

Type IA and IB topoisomerases cleave one strand of a ds nucleic acid molecule. Cleavage of a ds nucleic acid molecule by type IA topoisomerases generates a 5' phosphate and a 3' hydroxyl at the cleavage site, with the type IA topoisomerase covalently binding to the 5' terminus of a cleaved strand. In comparison, cleavage of a ds nucleic acid molecule by type IB topoisomerases generates a 3' phosphate and a 5' hydroxyl at the cleavage site, with the type IB topoisomerase covalently binding to the 3' terminus of a cleaved strand. Type IA topoisomerases include, for example, *E. coli* topoisomerase I and topoisomerase III, eukaryotic topoisomerase II, and archeal reverse gyrase (see Berger, *Biochim. Biophys. Acta* 1400:3-18, 1998, which is incorporated herein by reference).

Type IB topoisomerases include the nuclear type I topoisomerases present in all eukaryotic cells and those encoded by Vaccinia and other cellular poxviruses (see Cheng et al., *Cell* 92:841-850, 1998, which is incorporated herein by reference). The eukaryotic type IB topoisomerases are exemplified by those expressed in yeast, *Drosophila* and mammalian cells, including human cells (see Caron and Wang, *Adv. Pharmacol.* 29B:271-297, 1994; Gupta et al., *Biochim. Biophys. Acta* 1262:1-14, 1995, each of which is incorporated herein by reference; see, also, Berger, 1998, supra). Viral type IB topoisomerases are exemplified by those produced by the vertebrate poxviruses (Vaccinia, Shope fibroma virus, ORF virus, fowlpox virus, and molluscum contagiosum virus), and the insect poxvirus (*Amsacta moorei* entomopoxvirus) (see Shuman, *Biochim. Biophys. Acta* 1400:321-337, 1998; Petersen et al., *Virology* 230:197-206, 1997; Shuman and Moss, *Proc. Natl. Acad. Sci., USA* 84:7478-7482, 1987; Shuman and Prescott (1990) *J Biol Chem* 265(29):17826-36; Shuman, *J. Biol. Chem.* 269:32678-32684, 1994; U.S. Pat. No. 5,766,891; PCT/US95/16099; PCT/US98/12372, each of which is incorporated herein by reference; see, also, Cheng et al., 1998, supra).

Type II topoisomerases include, for example, bacterial gyrase, bacterial DNA topoisomerase IV, eukaryotic DNA topoisomerase II, and T-even phage encoded DNA topoisomerases (Roca and Wang, *Cell* 71:833-840, 1992; Wang, *J. Biol. Chem.* 266:6659-6662, 1991, each of which is incorporated herein by reference; Berger, 1998, supra). Like the type IB topoisomerases, the type II topoisomerases have both cleaving and ligating activities. In addition, like type IB topoisomerase, substrate ds nucleic acid molecules can be prepared such that the type II topoisomerase can form a covalent linkage to one strand at a cleavage site. For example, calf thymus type II topoisomerase can cleave a substrate ds nucleic acid molecule containing a 5' recessed topoisomerase recognition site positioned three nucleotides from the 5' end, resulting in dissociation of the three nucleic acid molecule 5' to the cleavage site and covalent binding of the topoisomerase to the 5' terminus of the ds nucleic acid molecule (Andersen et al. (1991) *J Biol Chem* 266:9203-9210). Furthermore, upon contacting such a type II topoisomerase-charged ds nucleic acid molecule with a second nucleic acid molecule containing a 3' hydroxyl group, the type II topoisomerase can ligate the sequences together, and then is released from the recombinant nucleic acid molecule. As such, type II topoisomerases also are useful for performing methods of the invention.

Mutation analysis of Vaccinia type IB topoisomerase reveals a large number of amino acid residues that can be mutated without affecting the activity of the topoisomerase, and has identified several amino acids that are required for activity (Shuman, 1998, supra). In view of the high homology shared among the Vaccinia topoisomerase catalytic domain and the other type IB topoisomerases, and the detailed mutation analysis of Vaccinia topoisomerase, it will be recognized that isolated catalytic domains of the type IB topoisomerases and type IB topoisomerases having various amino acid mutations can be used in the methods provided herein, and thus are considered to be topoisomerases for purposes of the present invention.

Figure 3:
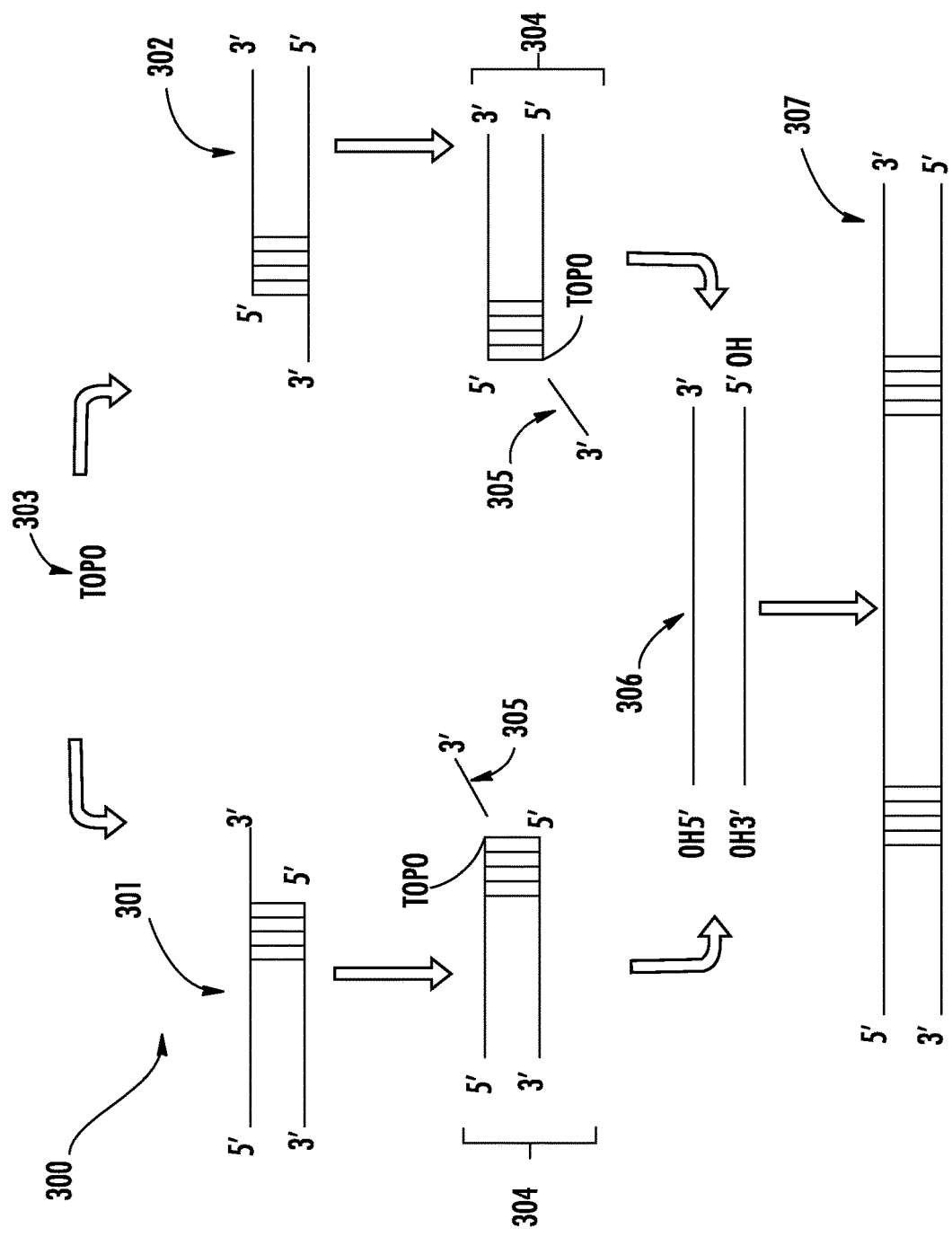
FIG. 3 illustrates an exemplary process (300) for preparing a TOPO-adaptor-target DNA duplex-TOPO-adaptor complex using a set of two complementary linear pro-adaptors. Reference is made to Example 1.

In one aspect, pro-adaptors carrying a consensus topoisomerase recognition sequence, e.g., (T/C)CCTTN (SEQ ID NOs: 12 and 13), are activated using vaccinia virus topoisomerase I (TOPO-I). FIG. 3 illustrates an example of the process (300) whereby linear pro-TOPO adaptors (301) and (302) are activated by a TOPO-I (303). In reference to FIG. 3, the TOPO-I, e.g., Vaccinia TOPO-I, binds and cleaves adaptor duplex DNA at the specific pentapyrimidine sequence e.g. 5'-CCCTT-3' (SEQ ID NO:11), shown by the base pairing vertical lines. Cleavage occurs by a transesterification reaction in which the CCCTT↓N phosphodiester is attacked by the active site tyrosine (e.g., Tyr-274) resulting in the formation of a DNA-(3'-phosphotyrosyl) protein adduct (304) and release of the 3'-overhang (305). Cleavage can occur with small CCCTT-containing oligonucleotides as long as there are at least six nucleotides upstream and two nucleotides downstream of the scissile phosphate (Shuman (1991) *J Biol Chem* 266: 11372-79). In the presence of the heterologous acceptor DNA 5' end of the DNA sample duplex (306), the covalently bound topoisomerase catalyzes a variety of DNA strand transfer reactions. It can either religate the CCCTT-containing strand across the same bond originally cleaved (as occurs during the relaxation of supercoiled DNA) or it can ligate the strand to a heterologous acceptor DNA 5' end, thereby creating a recombinant nucleic acid molecule, i.e., a TOPO-adaptor-target DNA duplex-TOPO-adaptor complex (307). An irreversible or "suicide" cleavage occurs when the CCCTT-containing substrate contains no more than fifteen base pairs 3' of the scissile bond, because the short leaving strand (305) dissociates from the protein-DNA complex. The suicide intermediate can transfer the incised CCCTT strand to DNA acceptor with a free 5'-OH, to yield an intermolecular ligation product. To assure covalent attachment of the Vaccinia topoisomerase to the acceptor duplex DNA during formation of the activated TOPO-adaptor (and prevent religation of the cleaved strand), the 5' end of the second nucleotide in the duplex strand of the pro-adaptor (shown in FIG. 3) is phosphorylated at the 5' end thereof, driving the reaction towards the cleaved product. Once the Vaccinia topoisomerase enzyme is covalently attached to the adaptor and the leaving group is separated from the pro-adaptor, the reaction is virtually quantitative and irreversible until an acceptor DNA is provided (i.e., a duplex DNA having a 5'-OH group).

Additionally, a vaccinia topoisomerase I-activated DNA intermediate can be religated to the 5'-OH end of an RNA molecule, thereby allowing rapid formation of DNA-RNA covalent adducts (see WO 98/56943). Accordingly, in addition to linking activated TOPO-adaptors to duplex DNA, in some embodiments, the activated TOPO-adaptors provided herein can be applied to the coupling of adaptors to RNA molecules with a free 5'-OH moiety.

Activated topoisomerase adaptor sequences and the precursor pro-TOPO adaptors exclude functional sequences that are typically included in adaptor sequences found in vectors used in molecular cloning methods that replicate sample DNA molecules in a host organism. "Cloning" herein refers to a method that involves the replication of one molecule to produce a population of cells with identical DNA molecules. Molecular cloning generally uses DNA sequences from two different organisms: the species that is the source of the DNA to be cloned, and the species that will serve as the living host for replication of the recombinant DNA. Thus, the activated topo-adaptors provided herein enable vector-independent manipulation, e.g., sequencing, of sample DNA. In certain embodiments, functional sequences that are excluded from the sequences of the adaptors provided herein include promoter sequences, enhancer sequences, transcription initiation sequences, polyadenylation signals, intronic sequences, translation initiation sequences, epitope tag sequences, integration-promoting factor sequences, mRNA stability-regulating sequences, restriction endonuclease recognition/cleavage sequences, synthetic multiple cloning site sequences, and cellular localization encoding sequences.

Preparation of Sequencing Libraries Using Activated TOPO Adaptors

In general, ligation of the TOPO adaptors to target duplex DNA molecules provides the target DNA an annealing site for a primer, i.e., an adaptor-specific primer, for the purposes of performing amplification and/or sequencing of the linked target DNA duplex. Consequently, all or any part of the oligonucleotides in the TOPO-adaptor can serve as an annealing site for one or more adaptor-specific primers used in the methods as described herein.

Several of the new methods employed for high throughput DNA sequencing (*Nature.* 437, 376-380 (2005); *Science.* 309, 5741, 1728-1732 (2005)) rely on a universal amplification reaction, whereby a DNA sample is randomly fragmented, then treated such the ends of the different fragments all contain the same DNA sequence. Fragments with universal ends can be amplified in a single reaction with a single pair of amplification primers.

In common with all amplification techniques, e.g., solid-phase bridging amplification used in Illumina sequencing, use of forward and reverse amplification primers is required, which primers include 'template-specific' nucleotide sequences which are capable of annealing to sequences in the template to be amplified, or the complement thereof, under the conditions of the annealing steps of the amplification reaction. The sequences in the template to which the primers anneal under conditions of the amplification reaction are referred to herein as 'primer-binding' sequences. Certain embodiments of the methods described in WO 98/44151 and WO 00/18957 make use of 'universal' primers to amplify templates comprising a variable template portion that it is desired to amplify flanked 5' and 3' by common or 'universal' primer binding sequences. The 'universal' forward and reverse primers include sequences capable of annealing to the 'universal' primer binding sequences in the template construct. The variable template portion, or 'target,' may itself be of known, unknown or partially known sequence. This approach has the advantage that it is not necessary to design a specific pair of primers for each target sequence to be amplified; the same primers can be used for amplification of different templates provided that each template is modified by addition of the same universal primer-binding sequences to its 5' and 3' ends. The variable target sequence can therefore be any DNA fragment of interest. An analogous approach can be used to amplify a mixture of templates (targets with known ends), such as a plurality or library of target nucleic acid molecules (e.g., genomic DNA fragments), using a single pair of universal forward and reverse primers, provided that each template molecule in the mixture is modified by the addition of the same universal primer-binding sequences.

Such 'universal primer' approaches to PCR amplification are advantageous since they enable multiple template molecules of the same or different, known or unknown sequence to be amplified in a single amplification reaction, which may be carried out on a solid support bearing a single pair of 'universal' primers. Simultaneous amplification of a mixture of templates of different sequences would otherwise require a plurality of primer pairs, each pair being complementary to each unique template in the mixture. The generation of a plurality of primer pairs for each individual template is not a viable option for complex mixtures of templates that are sequenced, for example, by NGS methods.

A single adaptor or two different adaptors may be linked to the target DNA duplex.

In some embodiments, two different activated TOPO adaptors are linked to the ends of the target DNA duplex. The two different adaptors are each formed by two oligonucleotides that are essentially complementary to each other throughout their length to provide a linear complementary adaptor that comprises a topoisomerase recognition sequence and at least one oligonucleotide primer binding sequence. The first of the two different activated linear adaptors differs from the second activated linear adaptor by the oligonucleotide primer binding sequence. For example, in reference to FIG. 1, in one embodiment, the first adaptor comprises a first oligonucleotide primer binding sequence e.g., SEQ ID NO:7, that is preferably fully complementary to a first oligonucleotide primer, e.g., SEQ ID NO:9; and the second adaptor comprises a second oligonucleotide primer binding sequence e.g., SEQ ID NO:8, that is preferably fully complementary to a second oligonucleotide primer, e.g., SEQ ID NO:10. Extension of the first primer annealed to the first primer binding sequence on the first adaptor provides an extension product that comprises a sequence that is complementary to the top strand of the target DNA duplex, and extension of the second primer annealed to the second primer binding sequence on the second adaptor provides an extension product that comprises a sequence that is complementary to the bottom strand of the target DNA duplex.

Figure 4:
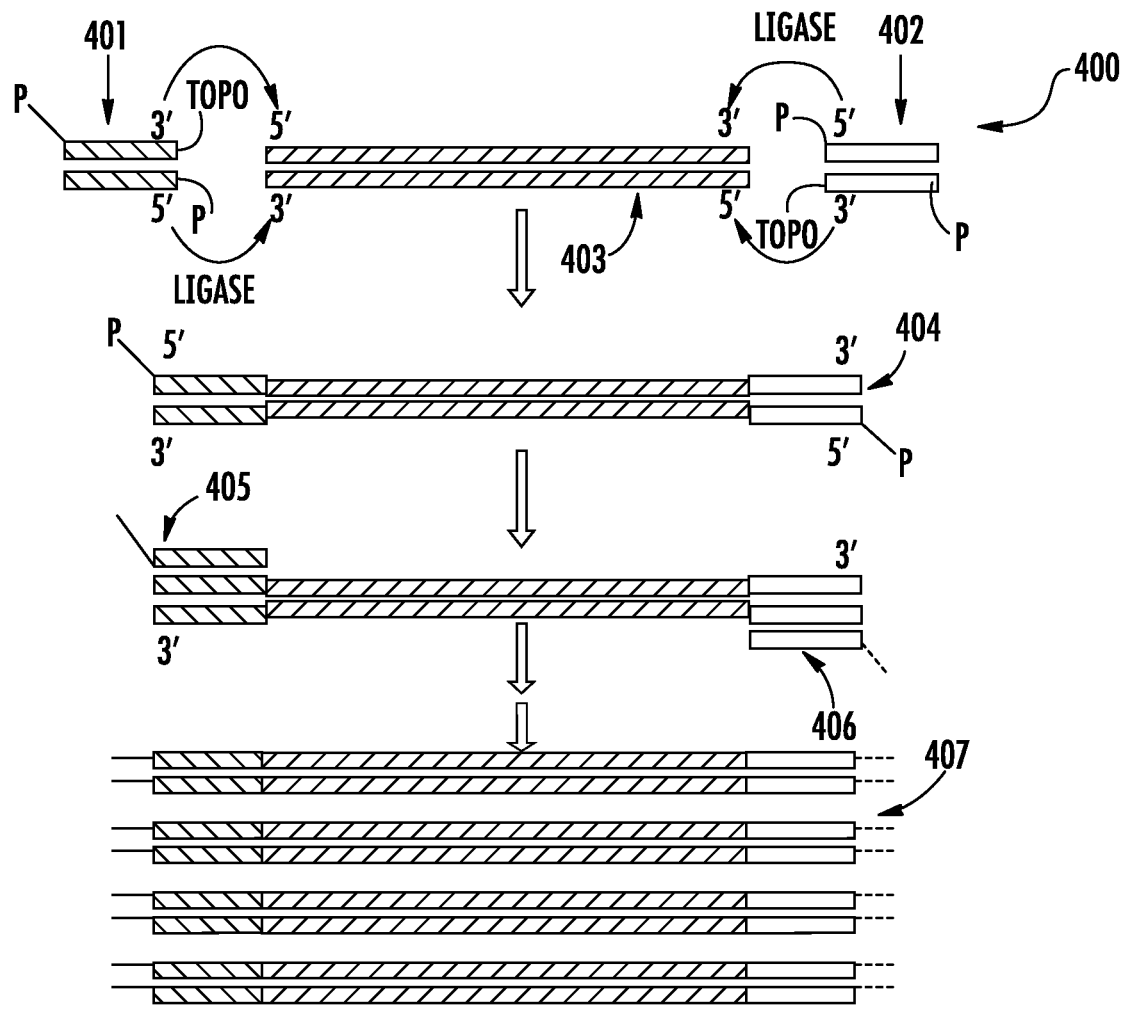
FIG. 4 illustrates an exemplary process (400) for preparing a library of target DNA duplexes for NGS sequencing using activated linear TOPO-adaptors.

FIG. 4 illustrates a process (400) for preparing a sequencing library using a set of activated complementary linear adaptors (401) and (402) e.g., the adaptors shown in FIG. 1. In reference to FIG. 4, first (401) and second (402) activated linear TOPO adaptors are linked to the first and second end of the target DNA duplex (403). As described elsewhere herein, the first activated adaptor comprises a first primer binding sequence, and the second activated adaptor comprises a second primer binding sequence. The two primer binding sequences are different from each other. Both first and second activated adaptors comprise a TOPO enzyme that is bound to the 3' end. The activated TOPO-adaptors are incubated with the blunt-ended and dephosphorylated target DNA duplex (403) in the presence of a DNA ligase e.g., T4 DNA ligase or T7 DNA ligase, which in combination with the activity of the TOPO enzyme bound to the 3'-end of each adaptor, covalently link the adaptors to the target DNA duplex, and thereby provides a library of different TOPO-adaptor-target DNA-TOPO-adaptor complexes (404). The ligation of the 5'-end of the target DNA to the adaptor is mediated by the topoisomerase of the adaptor, and the ligation of the 3'-end of the target DNA is mediated by ligase. Optionally, in some embodiments, a first oligonucleotide primer (405) is annealed to at least a portion of a first binding primer sequence on a first adaptor; and a second oligonucleotide primer (406) is annealed to at least a portion of a second binding primer sequence on a second adaptor. Each primer can be extended by addition of nucleotides, and the extended product is amplified (407), e.g., by PCR, and sequenced.

In some embodiments, a single TOPO-adaptor is linked to both ends of the target DNA duplex. As described elsewhere herein, the single TOPO-adaptor is formed by an oligonucleotide comprised of 5' and 3' terminal regions that comprise a duplex stem region and a non-complementary region that forms a single-stranded loop, e.g., the hairpin adaptor shown in FIG. 2. The duplex stem region of the partially complementary adaptor comprises the topoisomerase recognition sequence, and at least one oligonucleotide primer binding sequences, e.g., amplification primer binding sequence, to which at least one primer is annealed and extended to provide an extension product that is complementary to at least one strand of each TOPO-adaptor-target DNA duplex construct. In some embodiments, a first primer binding sequence and a second primer sequence are separated by a uracil, which can be removed to open the loop portion and make it available for amplification e.g. PCR.

Figure 5:
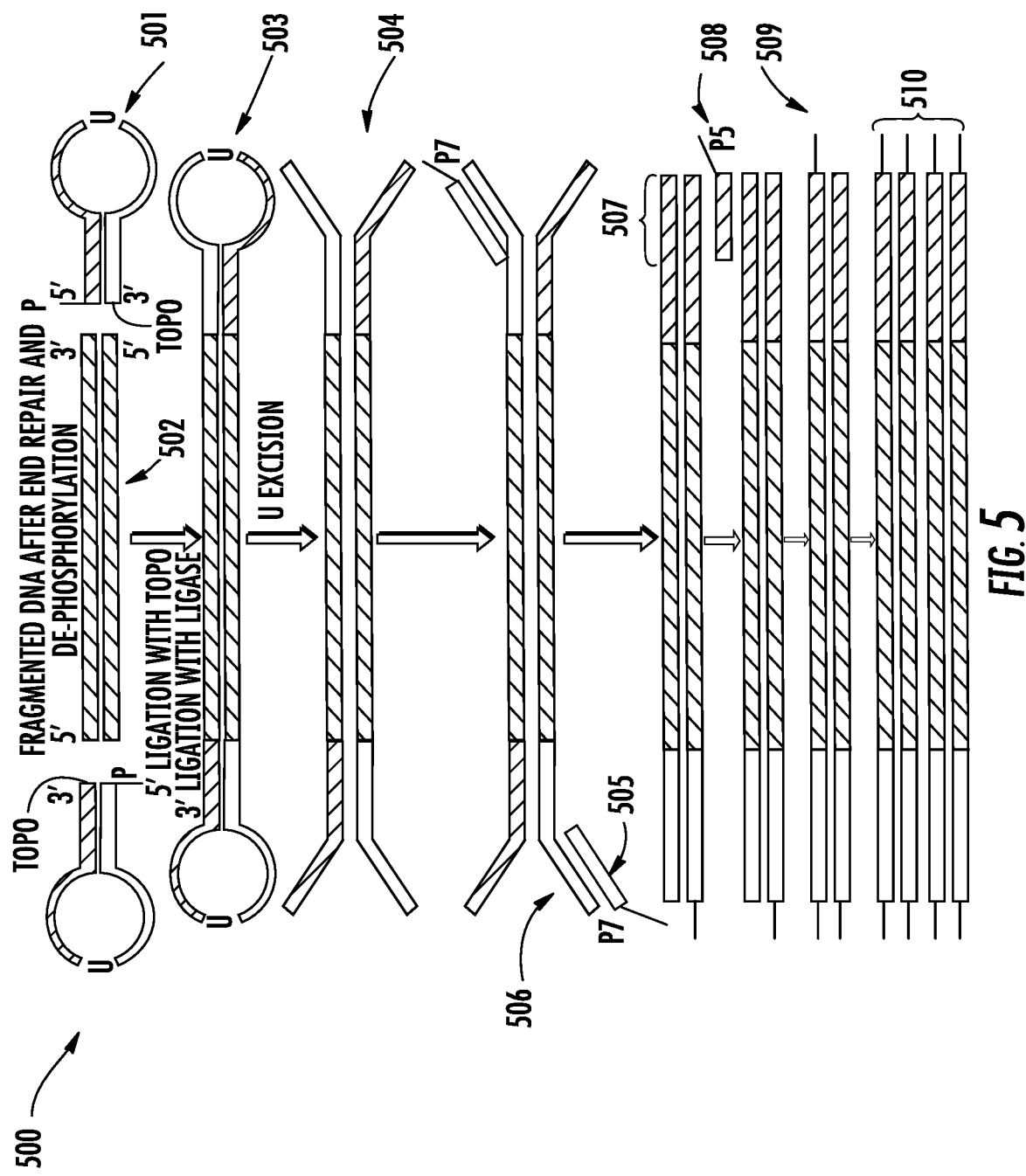
FIG. 5 illustrates an exemplary process (500) for preparing a library of target DNA duplexes for NGS sequencing using activated hairpin TOPO-adaptors.
Figure 6A:
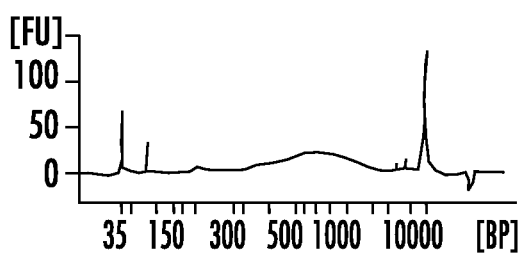
FIG. 6A-D shows exemplary electropherograms of a sample DNA sequencing library prepared using topoisomerase-dependent linkage of TOPO-activated to target DNA duplexes (6C) and (6D) as compared to using ligase-only dependent linkage of standard oligonucleotide adaptors (6A) and (6B).
Figure 6B:
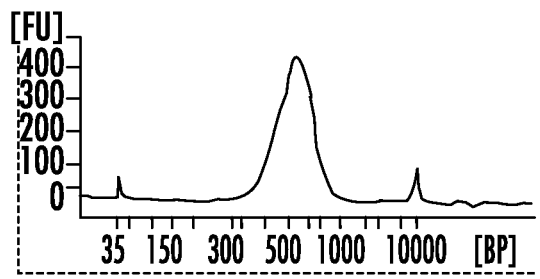
Figure 6C:
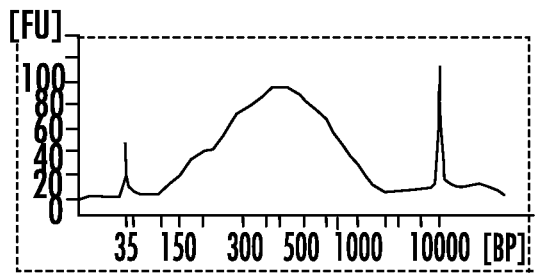
Figure 6D:
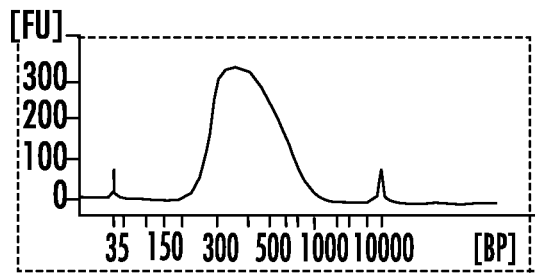

FIG. 5 illustrates an exemplary process (500) for preparing a sequencing library using the TOPO-activated partially complementary hairpin adaptor. For example, as shown in FIG. 5, following TOPO activation of the pro-adaptor shown in FIG. 2, a single blunt-ended partially complementary activated hairpin TOPO-adaptor oligonucleotide adaptor (501), e.g., SEQ ID NO:26, comprising the topoisomerase recognition sequence, e.g., CCCTT (SEQ ID NO:11), and a topoisomerase bound to the 3' end of the oligonucleotide, is linked to each end of a target DNA duplex (502). Linkage of the adaptors to the ends of the DNA duplex is obtained by incubating the activated hairpin adaptor with the blunt-ended and dephosphorylated target DNA duplex (502) in the presence of a DNA ligase, e.g., T4 DNA ligase or T7 DNA ligase, which in combination with the activity of the TOPO enzyme bound to the 3'-end of each adaptor, covalently links the adaptors to the target DNA duplex, and thereby provide a library of TOPO-adaptor-target DNA duplex-TOPO-adaptor complexes (503). The single oligonucleotide that forms the partially complementary TOPO adaptor comprises an oligonucleotide, e.g., SEQ ID NO:20, that separates the first primer binding sequence, e.g., SEQ ID NO: 21, from the second primer sequence, e.g. SEQ ID NO:22, and may include a recognition site, e.g., a uracil base, for a DNA glycosylase, e.g., Uracil DNA Glycosylase (UDG), and a DNA endonuclease, e.g., Endonuclease VIII. In some embodiments, the loop is not cleaved, e.g. by UDG and DNA endonuclease. An uncleaved loop TOPO-adaptor-target DNA duplex-TOPO-adaptor complex (503) can be subjected to rolling amplification and sequenced using real-time sequencing, e.g., via the Pacific Biosciences NGS platform. Alternatively, in some embodiments, the uracil base is removed by enzymatic digestion of the DNA by a mixture of UDG and endonuclease to open the loop portion of the partially complementary TOPO-adaptor and make it available for extension and/or amplification (504). The cleaved loop TOPO-adaptor-target DNA complex can be sequenced, for example, using other NGS platforms including those developed by Roche, Life Technologies, and ABI.

In one embodiment, and in reference to FIGS. 2 and 5, a first oligonucleotide primer (505), e.g., SEQ ID NO:24, is annealed to a first oligonucleotide primer binding sequence (506), e.g., SEQ ID NO:21, and is extended to provide an extension product that comprises the first universal adaptor sequence (505), e.g., SEQ ID NO:24, and a second primer binding sequence (507), e.g., SEQ ID NO:23. Subsequently, a second oligonucleotide primer (508), e.g., SEQ ID NO:25, can be annealed to the second primer binding sequence of (507), e.g., SEQ ID NO:23, and extended to provide a product (509) that comprises sequences of first and second universal adaptors. Thus, a library of TOPO-adaptor-target DNA-TOPO-adaptor complexes is generated. Optionally, amplification of the extension products can be performed to provide multiple copies of the target DNA (510).

Figure 9:
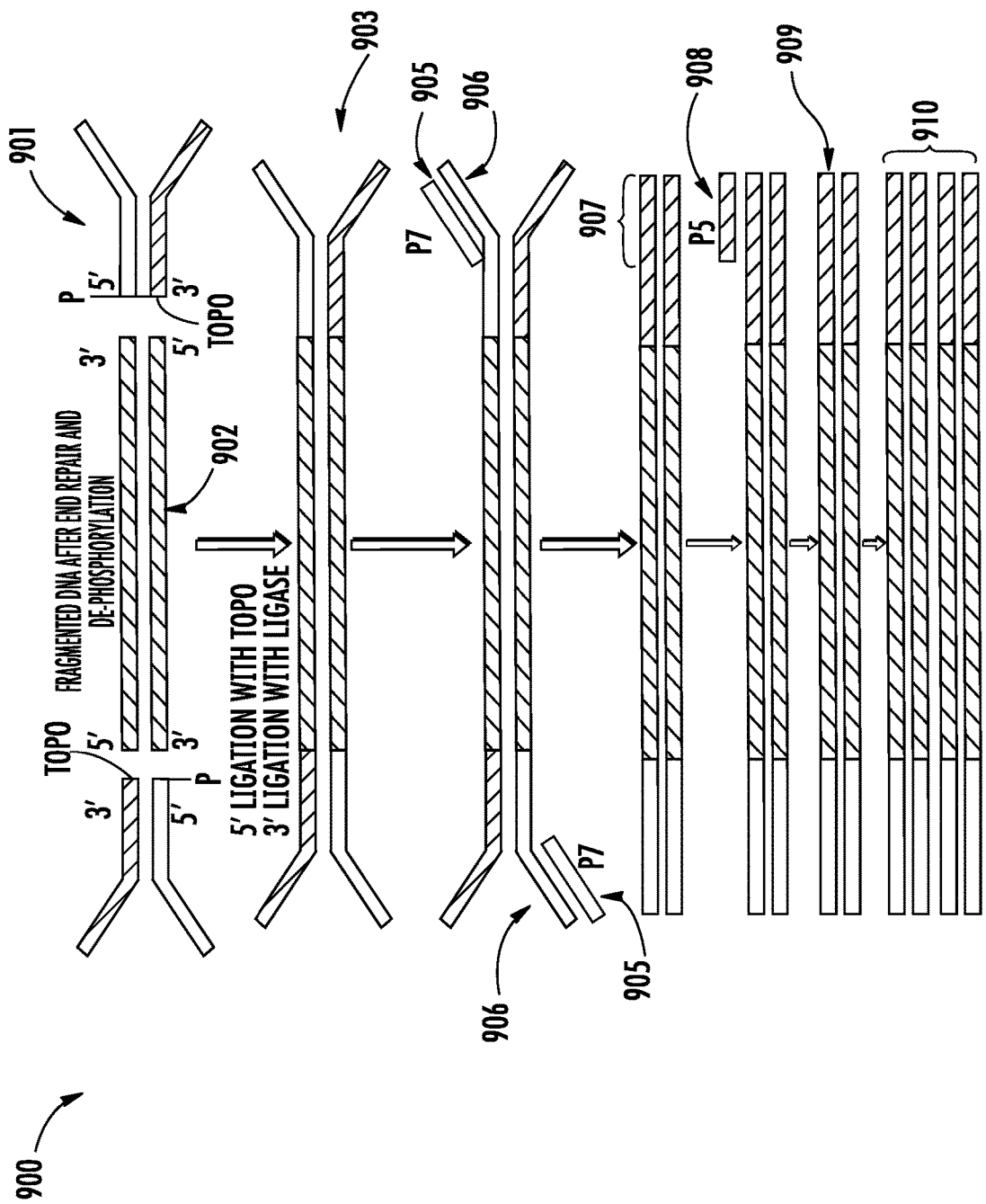
FIG. 9 illustrates an exemplary process (900) for preparing a library of target DNA duplexes for NGS sequencing using activated partially complementary TOPO-adaptors.

FIG. 9 illustrates an exemplary process (900) for preparing a sequencing library using the TOPO-activated partially complementary "Y-shaped" adaptor. For example, as shown in FIG. 9, following TOPO activation of the pro-adaptor shown in FIG. 7 or 8, a single blunt-ended partially complementary activated Y-shaped TOPO-adaptor oligonucleotide adaptor (901), comprising the topoisomerase recognition sequence, e.g., CCCTT (SEQ ID NO:11), and a topoisomerase bound to the 3' end of the oligonucleotide, is linked to each end of a target DNA duplex (902). Linkage of the adaptors to the ends of the DNA duplex is obtained by incubating the activated adaptor with the blunt-ended and dephosphorylated target DNA duplex (902) in the presence of a DNA ligase, e.g., T4 DNA ligase or T7 DNA ligase, which in combination with the activity of the TOPO enzyme bound to the 3'-end of each adaptor, covalently links the adaptors to the target DNA duplex, and thereby provides a library of TOPO-adaptor-target DNA duplex-TOPO-adaptor complexes (903).

In one embodiment, and in reference to FIGS. 7, 8, and 9, a first oligonucleotide primer (905), is annealed to a first oligonucleotide primer binding sequence (906), and is extended to provide an extension product that comprises the first universal adaptor sequence (905) and a second primer binding sequence (907), e.g., SEQ ID NO:23. Subsequently, a second oligonucleotide primer (908) can be annealed to the second primer binding sequence of (907) and extended to provide a product (909) that comprises sequences of first and second universal adaptors. Thus, a library of TOPO-adaptor-target DNA-TOPO-adaptor complexes is generated. Optionally, amplification of the extension products can be performed to provide multiple copies of the target DNA (910).

Those of skill in the art will appreciate that, in general, the oligonucleotide sequence of adaptor-specific primers used for adaptor-mediated PCR amplification and/or sequencing will be designed to hybridize to whatever particular second or third oligonucleotide is used in the duplex linker under the conditions used for conducting the adaptor-mediated PCR amplification and/or sequencing.

NGS Sequencing

The TOPO-adaptors provided herein, can be used for constructing NGS libraries for sequencing genomic DNA and RNA, which can be cellular or cell-free. NGS was developed from a demand for cheaper and faster sequencing methods following the 13-year long completion of the Human Genome Project. Since completion of the first human genome sequence, demand for cheaper and faster sequencing methods has increased greatly. This demand has driven the development of next-generation sequencing (NGS). NGS platforms perform massively parallel sequencing, during which millions of fragments of DNA from a single sample or from multiple different samples are sequenced in unison. Massively parallel sequencing technology facilitates high-throughput sequencing, which allows an entire genome to be sequenced in less than one day. Although each NGS platform is unique in how sequencing is accomplished, these platforms share a similar base methodology that includes template preparation, sequencing and imaging, and data analysis (Metzker M L (2010) Sequencing technologies—the next generation. *Nat Rev Genet* 11:31-46).

TOPO-adaptors provided herein can be used for preparing libraries from DNA samples for sequencing whole genomes, targeted regions within genomes (for example, exome sequencing), ChIP-seq experiments, or PCR amplicons follows the same general workflow. Embodiments of library preparation workflows that utilize activated TOPO adaptors for NGS analysis generally entail: (i) optional fragmentation of target polynucleotides, (ii) end-repair and dephosphorylation of the 5' ends, (iii) ligation of the activated TOPO adaptors adaptors, and (iv) optionally, a limited PCR amplification to enrich for product that has TOPO adaptor ligated to both ends (FIGS. 4, 5, and 9).

The sample comprising genomic nucleic acids to which the method described herein may be applied may a biological sample such as a tissue sample, a biological fluid sample, or a cell sample, and processed fractions thereof. A biological fluid sample includes, as non-limiting examples, blood, plasma, serum, sweat, tears, sputum, urine, ear flow, lymph, interstitial fluid, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the source sample is a sample that is easily obtainable by non-invasive procedures, e.g., blood, plasma, serum, sweat, tears, sputum, urine, ear flow, and saliva. Preferably, the biological sample is a peripheral blood sample, or the plasma and serum fractions. In other embodiments, the biological sample is a swab or smear, a biopsy specimen, or a cell culture. In another embodiment, the sample is a mixture of two or more biological samples, e.g., a biological sample comprising two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In some embodiments, samples can be obtained from sources, including, but not limited to, samples from different individuals, different developmental stages of the same or different individuals, different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, or individuals with predisposition to a pathology, individuals with exposure to a pathogen such as an infectious disease agent (e.g., HIV), and individuals who are recipients of donor cells, tissues and/or organs. In some embodiments, the sample is a sample comprising a mixture of different source samples derived from the same or different subjects. For example, a sample can comprise a mixture of cells derived from two or more individuals, as is often found at crime scenes. In one embodiment, the sample is a maternal sample that is obtained from a pregnant female, for example a pregnant woman. In this instance, the sample can be analyzed using the methods described herein to provide a prenatal diagnosis of potential fetal disorders. Unless otherwise specified, a maternal sample comprises a mixture of fetal and maternal DNA, e.g., cfDNA. In some embodiments, the maternal sample is a biological fluid sample, e.g., blood sample. In other embodiments, the maternal sample is a purified cfDNA sample.

A sample can be an unprocessed biological sample, e.g., a whole blood sample. A source sample can be a partially processed biological sample, e.g., a blood sample that has been fractionated to provide a substantially cell-free plasma fraction. A source sample can be a biological sample containing purified nucleic acids, e.g., a sample of purified cfDNA derived from an essentially cell-free plasma sample. Processing of the samples can include freezing samples, e.g., tissue biopsy samples, fixing samples e.g. formalin-fixing, and embedding samples, e.g., paraffin-embedding. Partial processing of samples include sample fractionation, e.g., obtaining plasma fractions from blood samples, and other processing steps required for analyses of samples collected during routine clinical work, in the context of clinical trials, and/or scientific research. Additional processing steps can include steps for isolating and purifying sample nucleic acids. Further processing of purified samples includes, for example, steps for the requisite modification of sample nucleic acids in preparation for sequencing. Preferably, the sample is an unprocessed or a partially processed sample.

Samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue or cells.

Biological samples can be obtained from a variety of subjects, including but not limited to, human beings, and other organisms, including mammals, plants, or cells from the subjects, or microorganisms (e.g., bacteria, fungi).

Sample polynucleotides that can be analyzed as described herein comprise genomic cellular DNA, cell-free DNA (cfDNA), mitochondrial DNA, RNA, and cDNA. Preparation of sequencing libraries for some NGS sequencing platforms require that the polynucleotides be of a specific range of fragment sizes, and require that large polynucleotides, e.g., cellular genomic DNA be fragmented. Fragmentation of polynucleotide molecules by mechanical means cleaves the DNA backbone at C—O, P—O and C—C results in a heterogeneous mix of blunt and 3'- and 5'-overhanging ends with broken C—O, P—O and/C—C bonds (Alnemri and Litwack, *J Biol Chem* 265:17323-17333 [1990]; Richards and Boyer, *J Mol Biol* 11:327-340 [1965]) which need to be repaired for the subsequent enzymatic reactions, e.g., ligation of sequencing adaptors, that are required for preparing DNA for sequencing. Therefore, fragmentation of polynucleotides, e.g., cellular genomic DNA may be required. Alternatively, fragmentation of cfDNA, which exists as fragments of <300 base is not necessary for generating a sequencing library using cfDNA samples.

Once the starting DNA or cDNA has been fragmented, the fragments are blunted i.e. end-repaired and 5' dephosphorylated. Unlike most methods for preparing sequencing libraries for NGS, the TOPO adaptors provided herein do not require that the 3'-ends of the sample DNA be A-tailed. Next, the TOPO-adaptors are covalently linked to the sample DNA, i.e., target DNA duplex, as described above. The energy stored in the TOPO is released to join the 5'OH group of the sample DNA, and the 5' end of the second strand of the sample DNA is ligated to the 5'-phosphate group of the second strand of the adaptor. Covalent linking of TOPO adaptors to sample polynucleotides, e.g., DNA can be performed in a few minutes. The reaction takes less than 15 minutes, less than 10 minutes, or less than 5 minutes. Typically, only 5 minutes are required to covalently link the sample DNA to the TOPO adaptors. Following the ligation step, the TOPO-adaptor-target DNA duplex-TOPO adaptor complex can be amplified to enrich for the ligated product. In some embodiments, the amplification step comprises annealing an amplification primer that comprises an index sequence. In other embodiments, the amplification step completes the TOPO adaptor by adding a sequence complementary to a primer for solid-phase amplification. In yet other embodiments, the PCR amplification step comprises adding both a sequence complementary to a primer for solid-phase amplification, and an index sequence. In other embodiments, different barcoded TOPO adaptors can be used with different DNA samples.

An index sequence within an adaptor specific primer can be used to introduce an index into an amplified target DNA duplex. Each adaptor specific primer will therefore contain a unique index that identifies its corresponding target polynucleotide. For example, target DNA derived from one sample can be distinguished from the target DNA that is derived from a different sample. Accordingly, a plurality of adaptor specific primers corresponding to a plurality of different target polynucleotides of different samples can be employed to amplify the plurality of different target polynucleotides and result in incorporation of the uniquely identifying index into each resulting amplicon species within the plurality of amplicons thus produced.

The index can be a unique nucleotide sequence that is distinguishable from other indices. It can also be distinguishable from other nucleotide sequences within plurality polynucleotides either by sequence or location within the target polynucleotide. A nucleotide index can be a random or a specifically designed nucleotide sequence. An index can be of any desired sequence length so long as it is of sufficient length to be unique nucleotide sequence within a plurality of indices in a population and/or within a plurality of polynucleotides that are being analyzed or interrogated. In some embodiments, an index is a polynucleotide or region within a polynucleotide ranging from about 6 to about 30 or about 8 to about 30 nucleotides. An index can be, for example, any of about 10, 11, 12, 13, 14, 15, 16, 17, 18, 19, 20, 21, 22, 23, 24, 25, 26, 27, 28, 29 or 30 nucleotides or longer. For example, an index can be any of about 35, 40, 45 or 50 nucleotides or longer.

FIG. 1 illustrates exemplary adaptor specific primers designed to incorporate indices into target polynucleotides. Amplification with an adaptor specific forward primer i.e. the forward primer exemplified by primer (104) shown in FIG. 1, and which comprises an index [i5], and an adaptor specific reverse primer, i.e., the reverse primer exemplified by primer (106) as shown in FIG. 1, and which comprises an index [i7] as illustrated therein, incorporates the indices into the amplified target DNA duplex.

Excluding the step of dA-tailing the sample DNA, and using topoisomerase to covalently link the TOPO adaptors to the sample DNA, significantly reduces the time required to prepare the sequencing library. In some embodiments, excluding the time for the PCR amplification, the time required for preparing a sequencing library from a DNA sample according to the method provided herein is about 1.5 hours, about 2 hours, or about 1.5 to about 2 hours, which is significantly less than the time it takes to prepare a sequencing library using standard oligonucleotide adaptors that are ligated to target DNA duplexes using only a ligase enzyme. For example, excluding the time it takes for PCR amplification, the Illumina TruSeq Nano DNA library preparation takes about 3.5 hours.

Sequencing methods that can be used to verify the integrity of a source sample comprise Next Generation Sequencing technologies, which allow multiple samples to be sequenced individually (i.e., singleplex sequencing) or as pooled samples as indexed target DNA molecules (i.e., multiplex sequencing) in a single sequencing run, and generate up to several hundred million reads of DNA sequences. Sequences of target nucleic acids, and of indexed target nucleic acids can be determined using Next Generation Sequencing Technologies (NGS) in which clonally amplified DNA templates or single DNA molecules, respectively, are sequenced in a massively parallel fashion (e.g., as described in Voelkerding et al., *Clin Chem* 55:641-658 [2008]; Metzker M, *Nature Rev* 11:31-46 [2010]). NGS technologies are sometimes subclassified as First, Second and Third Generation Sequencing (Pareek and Smoczynski, *J Appl Genetics* 52:413-435 [2011]). In addition to high-throughput sequence information, NGS provides quantitative information, in that each sequence read can be a countable "sequence tag" representing an individual clonal DNA template or a single DNA molecule. The sequencing technologies of NGS include without limitation pyrosequencing, sequencing-by-synthesis with reversible dye terminators, sequencing by oligonucleotide probe ligation and ion semiconductor sequencing.

The major steps involved in next generation sequencing technologies that are generically applicable to all of the current technologies are library choice/construction, preparation of libraries for sequencing, and massively parallel sequencing.

Some of the sequencing technologies that are available commercially, and which can be used to sequence TOPO-adaptor-target DNA complexes are described below.

In one embodiment, the present method can be applied to bioassays that use 454 sequencing (http://www.454.com/) (e.g. as described in Margulies, M. et al., *Nature* 437:376-380 [2005]). The overall approach for 454 is pyrosequencing based. The sequencing preparation begins with lengths of DNA (e.g., amplicons or nebulized genomic/metagenomic DNA) that have adaptors on either end, created by using PCR primers with adaptor sequences or by ligation; these are fixed to tiny beads (ideally, one bead will have one DNA fragment) that are suspended in a water-in-oil emulsion. An emulsion PCR step is then performed to make multiple copies of each DNA fragment, resulting in a set of beads in which each one contains many cloned copies of the same DNA fragment. A fiber-optic chip filled with a field of microwells, known as a PicoTiterPlate, is then washed with the emulsion, allowing a single bead to drop into each well. The wells are also filled with a set of enzymes for the sequencing process (e.g., DNA polymerase, ATP sulfurylase, and luciferase). At this point, sequencing-by-synthesis can begin, with the addition of bases triggering pyrophosphate release, which produces flashes of light that are recorded to infer the sequence of the DNA fragments in each well as each base type (A, C, G, T) is added.

In another embodiment, the present method can be applied to bioassays that use Illumina sequencers. Illumina produces the most widely used family of platforms. The technology was introduced in 2006 (www.illumina.com) and was quickly embraced by many researchers because a larger amount of data could be generated in a more cost-effective manner. Illumina sequencing is a sequencing-by-synthesis method, which differs from that of the 454 in two major ways: (1) it uses a flow cell with a field of oligos attached, instead of a chip containing individual microwells with beads, and (2) it does not involve pyrosequencing, but rather reversible dye terminators. The dye-termination approach resembles the "traditional" Sanger sequencing. It is different from Sanger, however, in that the dye terminators are reversible, so they are removed after each imaging cycle to make way for the next reversible dye-terminated nucleotide. Sequencing preparation begins with lengths of DNA that have specific adaptors on either end being washed over a flow cell filled with specific oligonucleotides that hybridize to the ends of the fragments. Each fragment is then replicated to make a cluster of identical fragments. Reversible dye-terminator nucleotides are then washed over the flow cell and given time to attach; the excess nucleotides are washed away, the flow cell is imaged, and the terminators are reversed so that the process can repeat and nucleotides can continue to be added in subsequent cycles.

In another embodiment, the present method can be applied to bioassays that use Applied Biosystems SOLiD process (http://solid.appliedbiosystems.com). The SOLiD process begins with an emulsion PCR step akin to the one used by 454, but the sequencing itself is entirely different from the previously described systems. Sequencing involves a multiround, staggered, dibase incorporation system. DNA ligase is used for incorporation, making it a "sequencingby-ligation" approach, as opposed to the "sequencing-by-synthesis" approaches mentioned previously. Mardis (Mardis E R., Next-generation DNA sequencing methods, *Annu Rev Genomics Hum Genet* 2008; 9:387-402) provides a thorough overview of the complex sequencing and decoding processes involved with using this system.

In another embodiment, the present method can be applied to bioassays that use the Ion Torrent system (http://www.iontorrent.com/). The Ion Torrent system begins in a manner similar to 454, with a plate of microwells containing beads to which DNA fragments are attached. It differs from all of the other systems, however, in the manner in which base incorporation is detected. When a base is added to a growing DNA strand, a proton is released, which slightly alters the surrounding pH. Microdetectors sensitive to pH are associated with the wells on the plate, which is itself a semiconductor chip, and they record when these changes occur. As the different bases (A, C, G, T) are washed sequentially through, additions are recorded, allowing the sequence from each well to be inferred.

In another embodiment, the present method can be applied to bioassays that use the PacBio single-molecule, real-time sequencing approach (http://www.pacificbiosciences.com/). The PacBio sequencing system involves no amplification step, setting it apart from the other major next-generation sequencing systems. The sequencing is performed on a chip containing many zero-mode waveguide (ZMW) detectors. DNA polymerases are attached to the ZMW detectors and phospholinked dye-labeled nucleotide incorporation is imaged in real time as DNA strands are synthesized. PacBio's RS II C2 XL currently offers both the greatest read lengths (averaging around 4,600 bases) and the highest number of reads per run (about 47,000). The typical "paired-end" approach is not used with PacBio, since reads are typically long enough that fragments, through CCS, can be covered multiple times without having to sequence from each end independently. Multiplexing with PacBio does not involve an independent read, but rather follows the standard "in-line" barcoding model.

In another embodiment, the present method can be applied to bioassays that use nanopore sequencing (e.g., as described in Soni G V and Meller A., *Clin Chem* 53: 1996-2001 [2007]). Nanopore sequencing DNA analysis techniques are being industrially developed by a number of companies, including Oxford Nanopore Technologies (Oxford, United Kingdom), Roche, and Illumina. Nanopore sequencing is a single-molecule sequencing technology whereby a single molecule of DNA is sequenced directly as it passes through a nanopore. Nanopore sequencing is an example of direct nucleotide interrogation sequencing, whereby the sequencing process directly detects the bases of a nucleic acid strand as the strand passes through a detector. A nanopore is a small hole, of the order of 1 nanometer in diameter Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Another example of direct nucleotide interrogation sequencing is that of Halcyon.

EXAMPLES

The present invention is described in further explained in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Preparation of Topoisomerase-Activated Sequencing Adaptors

Activated topoisomerase adaptors (TOPO adaptors) were prepared by hybridizing synthetic oligonucleotides (SEQ ID NOs: 1 and 2), and (SEQ ID NOs: 4 and 5). A first adaptor of the adaptor set was prepared by hybridizing a first oligonucleotide ACACTGTTTCACGACAGGTGTT-GATCCCTTATTCCGATAGTG (SEQ ID NO:1) to a second oligonucleotide AAGGGCGATCAACACCTGTCGT-GAAACAGTGT (SEQ ID NO:2). A second adaptor of the adaptor set was prepared by hybridizing a third oligonucleotide AAGGGGTGACTGGAGTTCAGACGTGTGCTATC (SEQ ID NO:4) to a fourth oligonucleotide GATAGCACACGTCTGAACTCCAGTCACCCCTTAT-TCCGATAGTG (SEQ ID NO:5). Hybridization of the oligonucleotides provides each adaptor with a single topoisomerase recognition sequence/site CCCTT (SEQ ID NO:11). The oligonucleotides (10 µM) were hybridized in 10 mM Tris-HCl (pH 7.5), 160 mM NaCl, and amplified in a thermal cycler for the following cycles: 98° C. for 5 minutes, 85° C. for 5 minutes, 72° C. for 5 minutes, 65° C. for 5 minutes, 55° C. for 5 minutes, 42° C. for 5 minutes, 37° C. for 15 minutes, 20° C. for 30 minutes, and then held at 20° C.

Topoisomerase was conjugated by mixing 50 µl of annealed oligonucleotides, 50 µl of 5×TOPO conjugation buffer at 1× concentration: 20 mM Tris-acetate, pH 7.9 @25° C., 50 mM Potassium Acetate, 10 mM Magnesium Acetate, 100 µg/ml BSA, 2.3 mM ATP, 100 µg Vaccinia Topoisomerase I (31.25 pmol/µg; 500 Units/pmol), 46 units T4 polynucleotide kinase (MCLAB product no. T4PK) and $H_2O$ to a final reaction volume of 200 µl. After a 90 minute incubation at 37° C., the activated topoisomerase adaptors were isolated by HPLC.

As Shown in FIG. 3, activation of the adaptors results in blunt ended-double stranded adaptors having Topoisomerase linked to the 3' ends. The top and bottom strands of the activated first adaptor have sequences SEQ ID NOs:3 and 2, respectively, and the top and bottom strands of the activated second adaptor have sequences SEQ ID NOs: 4 and 6, respectively.

Example 2

Preparation of a Sequencing Library Using Topoisomerase-Activated Adaptors

To demonstrate the advantages of using TOPO adaptors in preparing a sequencing library for massively parallel sequencing, equivalent amounts of fragmented sample DNA were used to prepare a sequencing library according the topoisomerase-based method provided in the disclosure, and a sequencing library in parallel compared to Illumina's method of library preparation using Illumina's ligase-only based method.

DNA Sample Preparation

Lambda DNA or human genomic DNA was sheared into fragments of mostly 350 bp using a Covaris M220 Focused-ultrasonicator. DNA sample (10-500 ng) was end-repaired for 15 minutes at 20° C. in a 50 µl reaction mixture containing 10 µl of 5× End-repair buffer (1× concentration: 20 mM Tris-acetate, pH 7.9 at 25° C., 50 mM potassium acetate, 10 mM magnesium acetate, 100 µg/ml bovine serum albumin (BSA)) containing 0.2-0.6 mM dNTPs, 3 µl of end-repair enzyme (T4 DNA Polymerase, MCLAB product no. T4DP, 9 units). The end-repair enzyme was heat-inactivated for 10 minutes at 75° C. The 5' phosphate groups of the DNA were dephosphorylated by adding 3 µl (30 units) of alkaline phosphatase (calf intestinal phosphatase (CIP)) for 10 minutes at 50° C.

The end-repaired-dephopshorylated sample DNA was purified by incubating the 53 µl reaction mixture with 80 µl of MCMag™ Purification Beads (MCLAB) (magnetic beads that bind to negatively-charged DNA under the conditions described in this example). The DNA sample was incubated with the beads for 5 minutes, and the bead-bound DNA was washed twice with ethanol. The beads were allowed to dry at room temperature. The DNA was then eluted from the beads for 5 minutes in elution buffer (0.1×TE buffer). 1×TE buffer is 10 mM Tris-HCl, pH 7.5, 1 mM EDTA.

Topoisomerase-Based Preparation of Sample DNA Sequencing Library

Fifteen microliters of purified end-repaired and dephosphorylated sample DNA were incubated with 3 µl of activated topoisomerase adaptor, prepared according to Example 1, 2 µl of T7 ligase, 1 µl ATP, 2.5 µl 10× Ligation buffer, in a 25 µl reaction mixture. The reaction mixture was incubated at room temperature for 5 minutes. The Adaptor-DNA-Adaptor complex was purified by incubating 25 µl of complex with 30 µl binding buffer and MCMag™ Purification Beads (MCLAB) for 5 minutes. The sample was washed twice with 80% ethanol, then eluted in 25 µl of elution buffer. The amount and quality of the adaptor-sample complex was verified on a Bioanalyzer.

Limited Cycle Amplification

Twenty-three microliters of purified adaptor-DNA sample complex were mixed with 25 µl of PCR master mix (KAPA Library Amplification Kit or 2×MCAmp™ Library Amplification Master Mix (MCLAB; product nos. LIBA-50 or LIBAP-50) and 2 µl of a 15 µM PCR primer mixture containing forward primer AATGATACGGCGAC-CACCGAGATCTACACACACTGTTT-CACGACAGGTGTTGATCG (SEQ ID NO:9) and reverse primer CAAGCAGAAGACGGCATACGAGATGA-TAGCACACGTCTGAACTCCAGTCAC (SEQ ID NO:10). FIG. 1 shows that PCR primer of SEQ ID NO:9 is complementary to the first primer binding sequence (SEQ ID:7) on the second strand of the first adaptor, and PCR primer of SEQ ID NO:10 is complementary to the second primer binding sequence (SEQ ID NO:8) on the second strand of the second adaptor. The DNA sample was amplified for 6-10 cycles.

The amplified product (35 µl) was bound to purification beads (42 µl; MCMag™ Purification Beads washed and eluted in 25 µl of 0.1×TE buffer The PCR product was analyzed by agarose gel electrophoresis and/or using a Bioanalyzer.

Ligase-Only-Based Preparation of Sample DNA Sequencing Library

One hundred nanograms of purified end-repaired and 3' adenylated sample DNA were incubated with Illumina's TruSeq adaptors, and ligated using ligase (provided by Illumina's TruSeq Nano DNA LT Library Prep Kit) according to Illumina's protocol. Ligation was performed for 10 minutes. In comparison, 100 ng of the purified end-repaired and dephosphorylated sample DNA, prepared as described above, were incubated with 2 microliters of purified TOPO-adaptors and 40 units ligase, and ligation was allowed to proceed for 5 minutes. The amount of ligation product, i.e., adaptor-sample DNA complex, obtained using the topoisomerase-based method provided by the disclosure was greater than that of the ligation product obtained using the ligase-only based method of Illumina. The exemplary data shown in FIG. 6 shows that the topoisomerase-based method yielded 3 times more adaptor-sample complex product than the amount obtained according to the ligase-only-based method of Illumina. Both library products were sequenced using Illumina's MiSeq sequencer. 100% coverage of the sample DNA was obtained for both libraries.

Additionally, the TOPO-based method could be performed in about half the time it took to prepare the Illumina library. The preparation time for the TOPO-based library was 120 minutes, while the preparation time when using commercial library preparations was between 155 and 210 minutes.

Therefore, topoisomerase-based preparation of sequencing libraries provides a more efficient method and a greater yield of library product than the gold-standard ligase-only based method that is widely used for preparing libraries for massively parallel sequencing.

Example 3

DNA Sample Preparation

Lambda DNA or human genomic DNA was sheared into fragments of mostly 350 bp using a Covaris M220 Focused-ultrasonicator. The DNA sample (10-500 ng) was dephosphorylated for 25 minutes at 50° C. in a 70 µl reaction mixture containing 10× End-repair buffer and 5 µl Alkaline Phosphatase (Shrimp Alkaline Phosphatase (5 units) or Antarctic Phosphatase (25 units)). The Alkaline Phosphatase was heat-inactivated for 10 minutes at 75° C. The dephosphorylated sample DNA was end-repaired for 5 minutes at 72° C. by adding 8 µl mixture of End-repair buffer, dNTPs and 2.5 µl (10 units) end-repair enzyme(s) (Pfu DNA polymerase and/or KOD DNA polymerase).

Topoisomerase-Based Preparation of Sample DNA Sequencing Library

The dephosphorylated and end-repaired sample DNA was incubated with 2 µl of activated topoisomerase adaptor, prepared according to Example 1, 2 µl of ligase (such as T4 DNA Ligase or T7 DNA Ligase), 1 µl ATP, 10× Ligation buffer, in a 100 µl reaction mixture. The reaction mixture was incubated for 15 minutes at 16° C. The Adaptor-DNA-Adaptor complex was size selected by incubating 100 µl of complex with 160 µl diluted MCMag Purification Beads (MCLAB) for 5 minutes. The supernatant was purified by incubating with 30 µl MCMag Purification Beads (MCLAB) for 5 minutes. The sample was washed twice with 80% ethanol, and then eluted in 25 µl of elution buffer. The amount and quality of the adaptor-sample complex was verified on a Bioanalyzer.

Limited Cycle Amplification

Twenty-three microliters of purified adaptor-DNA sample complex were mixed with 25 ul of PCR master mix (such as KAPA Library Amplification Kits or 2×MCAmp Library Amplification Master Mix (MCLAB)) and 2 µl of a 15 µM PCR primer mixture containing forward primer AATGA-TACGGCGACCACCGAGATCTACACTCTTTCCCTA-CACGA (SEQ ID NO:27) for single-indexing adaptor reverse primer CAAGCAGAAGACGGCATACGAGAT (SEQ ID NO:29). The DNA sample was amplified for 6-10 cycles.

The amplified product (35 µl) was bound to purification beads (42 µl; MCMag™ DNA library purification beads washed and eluted in 25 µl of 0.1×TE buffer as described above. The PCR product was analyzed by agarose gel electrophoresis and/or using a Bioanalyzer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Sequence Listing Free Text

```
Oligonucleotide 1 (top strand) for first linear
pro-TOPO-adaptor
                                       SEQ ID NO: 1
ACACTGTTTCACGACAGGTGTTGATCCCTTATTCCGATAGTG Oligonucleotide 2 (bottom strand) for first
linear pro-TOPO adaptor
                                       SEQ ID NO: 2
AAGGGCGATCAACACCTGTCGTGAAACAGTGT Oligonucleotide 1 (top strand) for first linear
activated TOPO-adaptor
                                       SEQ ID NO: 3
ACACTGTTTCACGACAGGTGTTGATCCCTT Oligonucleotide 1 (top strand) for second
linear pro-TOPO-adaptor
                                       SEQ ID NO: 4
AAGGGGTGACTGGAGTTCAGACGTGTGCTATC Oligonucleotide 2 (bottom strand) for second
linear pro-TOPO adaptor
                                       SEQ ID NO: 5
GATAGCACACGTCTGAACTCCAGTCACCCCTTATTCCGATAGTG Oligonucleotide 1 (bottom strand) for second
linear activated TOPO-adaptor
                                       SEQ ID NO: 6
GATAGCACACGTCTGAACTCCAGTCACCCCTT First primer binding sequence
                                       SEQ ID NO: 7
CGATCAACACCTGTCGTGAAACAGTGT Second primer binding sequence
                                       SEQ ID NO: 8
GTGACTGGAGTTCAGACGTGTGCTATC First oligonucleotide primer
                                       SEQ ID NO: 9
AATGATACGGCGACCACCGAGATCTACACACACTGTTTCACGACAGG
TGTTGATCG Second oligonucleotide primer
                                       SEQ ID NO: 10
CAAGCAGAAGAGGGCATACGAGATGATAGCCACAGTCTGAACTCCAG
TCAC Topo recognition sequence in adaptor of
FIGS. 1 and 2
                                       SEQ ID NO: 11
CCCTT Recognition sequence for topoisomerase I-
consensus sequence is underlined- N is any
nucleotide
                                       SEQ ID NO: 12
CCCTTN Recognition sequence for topoisomerase I-
consensus sequence is underlined- N is any
nucleotide
                                       SEQ ID NO: 13
TCCTTN Recognition sequence for topoisomerase I-
consensus sequence is underlined
                                       SEQ ID NO: 14
GCCCTTATTCCC Recognition sequence for topoisomerase I-
consensus sequence is underlined
                                       SEQ ID NO: 15
TCGCCCTTATTC Recognition sequence for topoisomerase I-
consensus sequence is underlined
                                       SEQ ID NO: 16
TGTCGCCCTTAT Recognition sequence for topoisomerase I-
consensus sequence is underlined
                                       SEQ ID NO: 17
GTGTCGCCCTTA Recognition sequence for topoisomerase I-
consensus sequence is underlined
                                       SEQ ID NO: 18
GATTCCCCTTATTCCGATAGTG Recognition sequence for topoisomerase I-
consensus sequence is underlined
                                       SEQ ID NO: 19
AAGGGCGATC Oligonucleotide for hairpin pro-TOPO-adaptor
                                       SEQ ID NO: 20
AAGGGCGATCAAGAGTTCAGACGTGTGCTATCUACACTGTTTCACGA
CAGGTGTTCATCGCCCTTATTCCGATAGTG First primer binding sequence in hairpin
adaptor
                                       SEQ ID NO: 21
CTATCGTGCAGACTTGAG Second primer sequence in hairpin loop
                                       SEQ ID NO: 22
ACACTGTTTCACGACAGGTG Second primer binding sequence in hairpin
adaptor is generated by extension of first
primer as reverse complement of SEQ ID NO: 22
                                       SEQ ID NO: 23
TCAAGACCTGTACTGAAACAGTGT First oligonucleotide primer for hairpin
adaptor
                                       SEQ ID NO: 24
CAAGCAGAAGACGGCATACGAGATGATGATAGCACACGTCTGAACTC
TTGA Second oligonucleotide primer for hairpin
adaptor
                                       SEQ ID NO: 25
AATGATACGACCACCGAGTCTACACACACTGTTTCACGACAGGTGTT
GA sequence of activated hairpin adaptor
                                       SEQ ID NO: 26
AAGGGCGATCAAGAGTTCAGACGTGTGCTATCUACACTGTTTCACGA
CAGGTGTTCATCGCCCTT
``` forward primer for single-indexing adaptor
SEQ ID NO: 27
AATGATACGGCGACCACCGAGATCTACACTCTTTCCCTACACGA forward primer for dual-indexing adaptor
SEQ ID NO: 28
AATGATACGGCGACCACCGAGATCTACAC reverse primer for single-indexing or dual-indexing adaptor
SEQ ID NO: 29
CAAGCAGAAGACGGCATACGAGAT pro-adaptor top strand for single indexing adaptor
SEQ ID NO: 30
AATGATACGGCGACCACCGAGATCTACACTCTTTCCCTACACGACGCGCGGCCGATGCCCGGAGGCCGATAGTG pro-adaptor bottom strand for single or dual indexing adaptor
SEQ ID NO: 31
GTTCGTCTTCTGCCGTATGCTCTACACTGACCTCAAGTCTGCACACGAGAAGGCTACGGGAA pro-adaptor top strand for dual indexing adaptor
SEQ ID NO: 32
AATGATACGGCGACCACCGAGATCTACACACACTCTTTCCCTACACGACGCTCTTCCGATGCCCTTATTCCGATAGTG first primer binding sequence for single or dual indexing adaptor
SEQ ID NO: 33
GTTCGTCTTCTGCCGTATGCTCTA complement of second binding sequence for single indexing adaptor
SEQ ID NO: 34
TCGTGTAGGGAAAGAGTGTAGATCTCGGTGGTCGCCGTATCATT complement of second binding sequence for dual indexing adaptor
SEQ ID NO: 35
GTGTAGATCTCGGTGGTCGCCGTATCATT

---

What is claimed is:

1. A kit comprising:
   (i) a plurality of topoisomerase (TOPO)-activated sequencing adaptors that comprise a DNA duplex comprising first and second strands and a bound TOPO at or near the 3' end of the first strand, wherein said plurality of TOPO-activated sequencing adaptors comprises:
      (a) a set of first and second linear adaptors, wherein said first linear TOPO-activated sequencing adaptor comprises complementary sequences SEQ ID NOs:2 and 3; and wherein said second linear TOPO-activated sequencing adaptor comprises complementary sequences SEQ ID NOs:4 and 6;
      (b) hairpin TOPO-activated sequencing adaptors comprising SEQ ID NO:20;
      (c) TOPO-activated sequencing adaptors comprising first and second oligonucleotides of sequences SEQ ID NOs: 30 and 31, respectively; and/or
      (d) TOPO-activated sequencing adaptors each comprising first and second oligonucleotides of sequences SEQ ID NOs: 32 and 31, respectively; and
   (ii) instructions for preparing a DNA sequencing library.

2. The kit of claim 1, further comprising:
   (iii) a ligase enzyme.

3. The kit of claim 1, wherein said plurality of TOPO-activated sequencing adaptors do not comprise functional sequences that are required for replication of a DNA sequence in a host organism.

4. The kit of claim 1, wherein said plurality of TOPO-activated sequencing adaptors (c) or (d) comprise partially complementary sequences, wherein the adaptors comprise a first oligonucleotide and a second oligonucleotide, wherein portions of each of the first and second oligonucleotides are complementary to one another and form the DNA duplex region, wherein the first oligonucleotide comprises the bound TOPO at or near the 3' end, wherein portions of each of the first and second oligonucleotides are single stranded and not complementary to one another, wherein the second oligonucleotide comprises a first primer binding sequence, and wherein the first oligonucleotide comprises the reverse complement of a second primer binding site.

5. The kit of claim 1, wherein said plurality of partially complementary TOPO-activated sequencing adaptors (b) comprise an oligonucleotide that comprises sequences that are complementary to one another and form the DNA duplex region, wherein the first strand of the duplex comprises the bound TOPO at or near the 3' end, and a single-stranded hairpin region, wherein the hairpin region comprises a first oligonucleotide primer binding sequence and the reverse complement of a second primer binding site.

6. The kit of claim 5, wherein the hairpin region of the adaptor comprises a uracil residue, and the kit further comprises uracil DNA deglycosylase (UDG).

7. The kit of claim 1, wherein said plurality of TOPO-activated sequencing adaptors (a) comprise first linear TOPO-activated sequencing adaptors and second linear TOPO-activated sequencing adaptors,
   wherein said first linear TOPO-activated sequencing adaptors comprise a first primer binding sequence and said second linear TOPO-activated sequencing adaptors comprise a second primer binding sequence, wherein said first primer binding sequence differs from said second primer binding sequence, and wherein said first primer binding sequence hybridizes to a first oligonucleotide primer, and said second primer binding sequence hybridizes to a second oligonucleotide primer.

\* \* \* \* \*

SEQUENCE LISTING

<160> NUMBER OF SEQ ID NOS: 35

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acactgtttc acgacaggtg ttgatccctt attccgatag tg                           42

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aagggcgatc aacacctgtc gtgaaacagt gt                                     32

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acactgtttc acgacaggtg ttgatccctt                                        30

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4 aagggtgtgac tggagttcag acgtgtgcta tc                32

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatagcacac gtctgaactc cagtcacccc ttattccgat agtg                44

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatagcacac gtctgaactc cagtcacccc tt                32

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgatcaacac ctgtcgtgaa acagtgt                27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtgactggag ttcagacgtg tgctatc                27

<210> SEQ ID NO 9
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatgatacgg cgaccaccga gatctacaca cactgtttca cgacaggtgt tgatcg                56

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 10
caagcagaag agggcatacg agatgatagc cacagtctga actccagtca c         51

<210> SEQ ID NO 11
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 ccctt                                                             5

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: a, c, t, g, unknown or other

<400> SEQUENCE: 12 cccttn                                                            6

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: a, c, t, g, unknown or other

<400> SEQUENCE: 13 tccttn                                                            6

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcccttattc cc                                                    12

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tcgcccttat tc                                                    12
```

```
<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgtcgccctt at                                                              12

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgtcgccct ta                                                              12

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gattcccctt attccgatag tg                                                   22

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aagggcgatc                                                                 10

<210> SEQ ID NO 20
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
aagggcgatc aagagttcag acgtgtgcta tcuacactgt ttcacgacag gtgttcatcg          60
cccttattcc gatagtg                                                         77

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
```
ctatcgtgca gacttgag                                                 18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acactgtttc acgacaggtg                                               20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcaagacctg tactgaaaca gtgt                                          24

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caagcagaag acggcatacg agatgatgat agcacacgtc tgaactcttg a            51

<210> SEQ ID NO 25
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aatgatacga ccaccgagtc tacacacact gtttcacgac aggtgttga              49

<210> SEQ ID NO 26
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
aagggcgatc aagagttcag acgtgtgcta tcuacactgt tcacgacag gtgttcatcg   60 ccctt                                                              65

<210> SEQ ID NO 27
<211> LENGTH: 44
<212> TYPE: DNA
<213> ORGANISM: Artificial Sequence
<220> FEATURE:

<223> OTHER INFORMATION: Description of Artificial Sequence: Synthetic
     primer

<400> SEQUENCE: 27
aatgatacgg cgaccaccga gatctacact ctttccctac acga            44

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 28
aatgatacgg cgaccaccga gatctacac                              29

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 29
caagcagaag acggcatacg agat                                   24

<210> SEQ ID NO 30
<211> LENGTH: 74
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 30
aatgatacgg cgaccaccga gatctacact ctttccctac acgacgcgcg gccgatgccc    60
ggaggccgat agtg                                              74

<210> SEQ ID NO 31
<211> LENGTH: 62
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 31
gttcgtcttc tgccgtatgc tctacactga cctcaagtct gcacacgaga aggctacggg    60
aa                                                           62

<210> SEQ ID NO 32
<211> LENGTH: 78
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 32
aatgatacgg cgaccaccga gatctacaca cactctttcc ctacacgacg ctcttccgat    60
gcccttattc cgatagtg                                          78

```
<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gttcgtcttc tgccgtatgc tcta                                           24

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcgtgtaggg aaagagtgta gatctcggtg gtcgccgtat catt                     44

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtgtagatct cggtggtcgc cgtatcatt                                      29
```